United States Patent [19]

Weichselbaum et al.

[11] Patent Number: 6,025,365
[45] Date of Patent: Feb. 15, 2000

[54] CHELERYTHRINE AND RADIATION COMBINED TUMOR THERAPY

[75] Inventors: Ralph Weichselbaum; Steven Chmura; Jose Quintans, all of Chicago, Ill.; Donald W. Kufe, Wellesley, Mass.

[73] Assignees: Arch Development Corp., Chicago, Ill.; Dana-Farber Cancer Institute, Boston, Mass.

[21] Appl. No.: 08/826,814

[22] Filed: Mar. 25, 1997

[51] Int. Cl.[7] .............................. A61N 43/42; A61N 5/00
[52] U.S. Cl. ................... 514/298; 514/280; 600/1
[58] Field of Search .................. 424/1.45, 1.65, 424/1.11; 534/10, 14; 514/298, 463, 468, 280, 279; 546/48, 108, 88; 600/1, 2, 3

[56] References Cited

U.S. PATENT DOCUMENTS

| 209,331 | 10/1878 | Daniel . | |
|---|---|---|---|
| 433,257 | 7/1890 | Ryan . | |
| 2,344,830 | 3/1944 | Mohs | 167/63 |
| 4,145,412 | 3/1979 | Ladanyi | 424/58 |
| 4,376,115 | 3/1983 | McCrorey | 424/145 |
| 4,406,881 | 9/1983 | Ladanyi | 424/49 |
| 4,599,228 | 7/1986 | Ladanyi | 424/52 |
| 5,137,912 | 8/1992 | Teng et al. | 514/463 |
| 5,324,520 | 6/1994 | Dunn et al. | 424/435 |
| 5,571,797 | 11/1996 | Ohno et al. | 514/44 |

FOREIGN PATENT DOCUMENTS

| WO 97/04761 | 2/1997 | WIPO . |
| WO 97/40844 | 11/1997 | WIPO . |

OTHER PUBLICATIONS

International Search Report dated Jul. 16, 1998 (PCT/US98/05842) (ARSB:517P).

Chmura et al., "Cross–talk between ceramide and PKC activity in the control of apoptosis," In: Mechanisms of Lymphocyte Activation and Immune Regulation VI, (eds Gupta, S. and Cohen, J.) Plenum Press, *Adv. Experi. Medicine Biol.*, 406:39–55, 1996.

Slesak et al., "In vitro effects of *Chelidonium majus* L. alkaloid thiophosphoric acid conjugates (Ukrain) on the phenotype of normal human lymphocytes," *Drugs Exptl. Clin. Res.* XVIII (Suppl.) 17–21, 1992.

Kleinrok et al., *Pol. J. Pharmacol. Pharm.*, 44:227–239, 1992.

Chmura et al., "Protein kinase C inhibition induces apoptosis and ceramide production through activation of a neutral sphingomyelinase," *Cancer Research*, 56:2711–2714, 1996.

Dewey et al., "Radiation–induced apoptosis: relevance to radiotherapy", *Int. J. Radiation Oncology Biol. Phys.*, 33(4):781–796, 1995.

Haimovitz–Friedman et al., "Ionizing radiation acts on cellular membranes to generate ceramide and initiate apoptosis," *J. Exp. Med.*, 180:525–35, 1994a.

Haimovitz–Friedman et al., Protein kinase C mediates basic fibroblast growth factor protection of endothelial cells against radiation–induced apoptosis, *Cancer Res.*, 54:2591–7, 1994b.

Herbert et al., "Chelerythrine is a potent and specific inhibitor of protein kinase C," *Biochem. Biophys. Res. Commun.*, 172:993–999, 1990.

Jarvis et al., "Induction of apoptosis and potentiation of ceramide–mediated cytotoxicity by sphingoid bases in human myeloid leukemia cells," *The Journal of Biological Chemistry*, 271(14):8275–8284, 1996.

Jarvis et al., "Ceramide and the induction of apoptosis," *Clinical Cancer Research*, 2:1–6, 1996.

Jarvis et al., "Induction of apoptotic DNA fragmentation and cell death in HL–60 human promyelocytic leukemia cells by pharmacological inhibitors of protein kinase C" *Cancer Research*, 54:1707–1714, 1994.

Hallahan et al., "Inhibition of Protein Kinases Sensitizes Human Tumor Cells to Ionizing Radiation," Radiation Research, 129, pp. 345–350, 1992 publication month not available.

Watson et al., "Radiosensitization of HL–60 human leukemis cells by bryostatin–1 in the absence of increased DNA fragmentation or apoptotic cell death," *Int. J. Radiat. Biol.*, 69(2):183–192, 1996.

Nakamura and Antoku, "Increase in postradiation survival of rat 3Y1 fibroblasts by a protein kinase inhibitor, staurosporine," *Cancer Biochem. Biophys.*, 14:15–21, 1994.

Findik et al., "Protein Kinase A Inhibitors Enchance Radiation–Induced Apoptosis," *Jouranl of Cellular Biochemistry*, 57:12–21, 1995.

Grant et al., "Modulation of 1–[β–D–Arabinofuranosyl] Cytosine–Induced Apoptosis in Human Myeloid Leukemia Cells by Staurosporine and Other Pharmacological Inhibitors of Protein Kinase C," *Oncology Research*, 6(2):87–99, 1994.

Kolesnick et al., "The sphingomyelin signal transduction pathway mediates apoptosis for tumor necrosis factor, Fas, and ionizing radiation," *Biochem. Cell Biol.*, 72:471–474, 1994.

Krongrad and Bai, "c–fos promoter insensitivity to phorbol ester and possible role of protein kinase C in androgen–independent cancer cells" *Cancer Research*, 54:6073–6077, 1994.

Ma et al., "Phosphorylation of the multidrug resistance associated protein gene encoded protein P190," *Biochemistry*, 34:3338–3343, 1995.

(List continued on next page.)

Primary Examiner—José G. Dees
Assistant Examiner—Michael G. Hartley
Attorney, Agent, or Firm—Arnold, White & Durkee

[57] ABSTRACT

Combination of low doses of irradiation and chelerythrine results in increased apoptosis in tumor cells. The doses of either irradiation or chelerythrine alone are such that increased apoptosis or decreased tumor growth or proliferation would not be expected.

66 Claims, 17 Drawing Sheets

OTHER PUBLICATIONS

Maity et al., "The molecular basis for cell cycle delays following ionizing radiation: a review," *Radiother. Oncol.,* 31:1–13, 1994.

Quintans et al., "Ceramide mediates the apoptotic response of WEHI 231 cells to anti–immunoglobulin, corticosteroids and irradiation," *Biochem. Biophys. Res. Commun.,* 202:710–4, 1994.

Rosenthal et al., "Phase I studies of continuous–infusion paclitaxel given with standard aggressive radiation therapy for locally advanced solid tumors," *Semin. Oncol.,* 22:13–17, 1995.

Sponsel et al., "Adenine nucleotide and protein kinase C regulation of renal tubular epithelial cell wound healing," *Kidney Int.,* 48:85–92, 1995.

Verheij et al., "Requirement for ceramide–initiated SAPK/JNK signalling in stress–induced apoptosis," *Nature,* 380:75–79, 1996.

Vokes and Weichselbaum, "Concomitant chemoradiotherapy: rationale and clinical experience in patients with solid tumors," *Journal of Clinical Oncology,* 8(5):911–934, 1990.

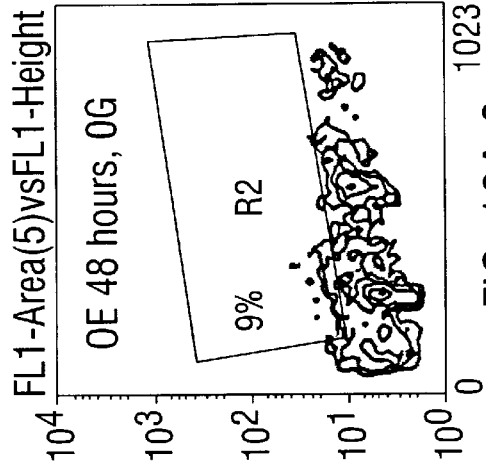
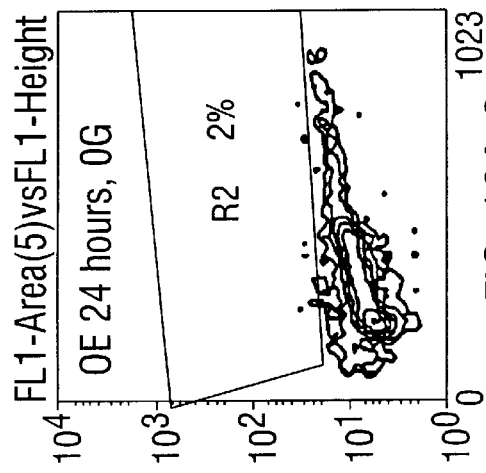
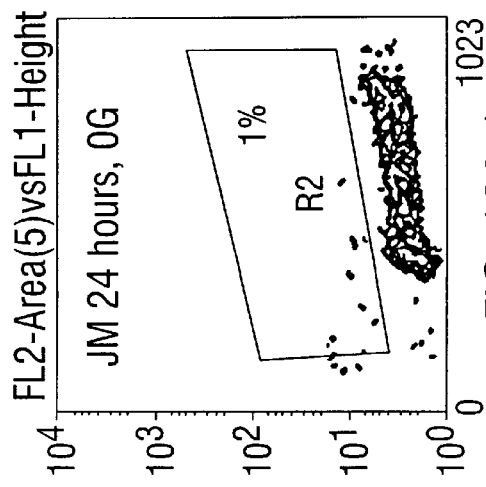
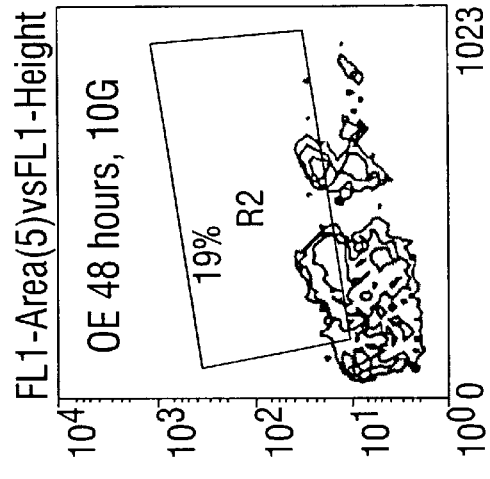
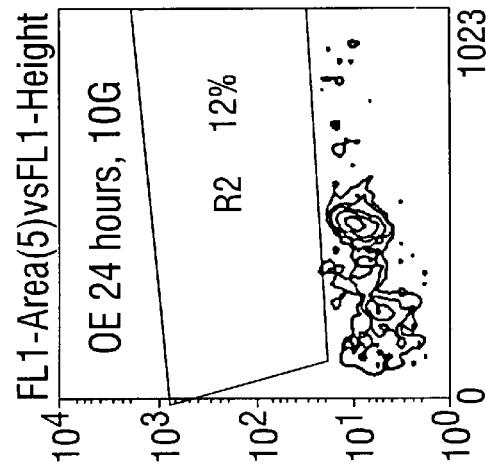
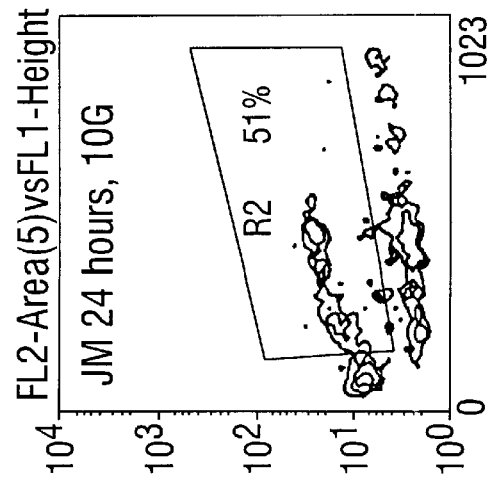

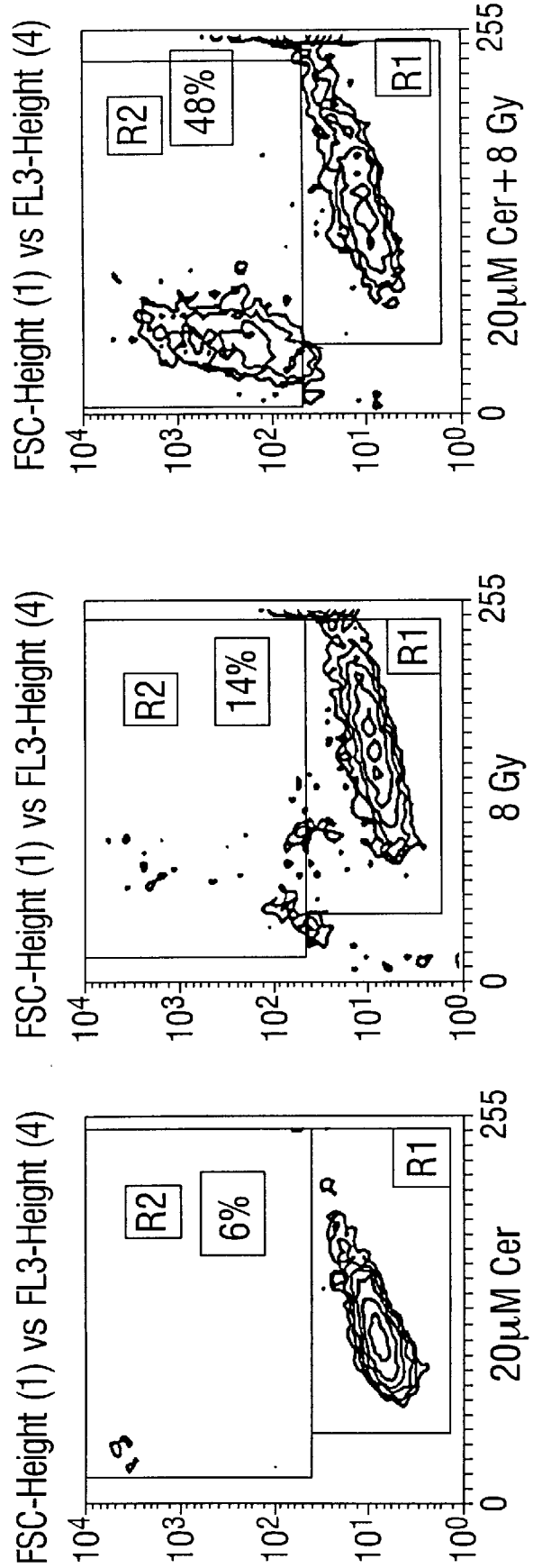

CHELERYTHRINE AND RADIATION COMBINED TUMOR THERAPY

The government owns rights in the present invention pursuant to grant number CA14068 from the National Institutes of Health.

BACKGROUND OF THE INVENTION

1. Field of the Invention

The present invention relates generally to the fields of cancer treatment and radiation therapy. More particularly, it concerns a combination of low doses of the protein kinase C (PKC) inhibitor chelerythrine with low doses of ionizing radiation to produce unexpectedly effective killing of radioresistant tumor cells.

2. Description of Related Art

Certain cancer treatment methods, including radiation therapy, involve damaging the DNA of the cancer cell. The cellular response to DNA damage includes activation of DNA repair, cell cycle arrest and lethality (Hall, 1988). Ionizing radiation (IR; x-irradiation) mediated killing of mammalian cells is frequently characterized by loss of reproductive integrity after one or more cell divisions (Chang and Little, 1992a, 1991, 1992b; Bussink et al., 1996). The induction of DNA double-strand breaks results in lethal chromosomal aberrations that include deletions, dicentrics, rings, and anaphase bridges (Hall, 1994). The morphological characteristics of cells dying a mitotic death following IR exposure include, as in necrotic death, multi-nucleated giant cells, cell-cell fusions (Hall, 1994), as well as the loss of membrane integrity (Quintans et al., 1994; Maity et al., 1994; Harmon and Allan, 1988; Radford and Murphy, 1994). In contrast to necrotic death, morphological characteristics of apoptosis induced by IR (Quintans et al., 1994; Maity et al., 1994; Harmon and Allan, 1988; Radford and Murphy, 1994) include activation of a genetic program that may be initiated by cytoplasmic or nuclear events which results in cytoplasmic blebbing, chromatin condensation, and DNA fragmentation (Jacobson et al., 1994; Raff et al., 1994).

Studies in tumor systems suggest that increasing the fraction of tumor cells undergoing apoptosis enhances tumor regression and tumor cures by IR (Meyn et al., 1993; 1994; 1995; Martin and Green, 1994; Indap and Rao, 1995; Dewey et al., 1995; Lowe et al., 1993b; Stephens et al., 1991; 1993). Agents which damage DNA, interfere with DNA repair, or alter cell-cycle checkpoints have been employed in human studies to modify the radiation tumor response with limited clinical success (Hall, 1988; Vokes and Weichselbaum, 1990; Rosenthal et al., 1995). Probably in part because loss of the apoptotic response to x-irradiation has been linked to a radiation resistant phenotype. Tumor radioresistance may occur through activation of DNA repair genes and cell cycle checkpoints (Maity et al., 1994; Sanchez and Elledge, 1995; Szumiel, 1994; Park, 1995; Shen et al., 1996; McKenna et al., 1991). For example, loss of p53 function is associated with a radioresistant phenotype as a consequence of a diminished ability to undergo apoptosis (Boise et al., 1995) and is often associated with treatment resistance and tumor relapse (Lowe et al., 1993a; 1993b; 1994). An increased ratio of anti-apoptotic to pro-apoptotic proteins also decreases IR-induced apoptosis.

Sphingomyelinase activation and subsequent ceramide production has been demonstrated to precede x-ray-induced apoptosis in several cell types (Quintans et al., 1994; Haimovitz-Friedman et al., 1994; Verheij et al., 1996; Kolesnick, 1994; Jarvis and Kolesnick, 1996; Santana et al., 1996). The loss of ceramide production following x-rays has recently been shown to confer a radioresistant phenotype in cells derived from acidic sphingomyelinase knockout mice and in tumor cells selected for a defect in neutral sphingomyelinase production. In addition, chelerythrine chloride (Herbert et al., 1990) and calphostin C (Kobayashi et al., 1989b), inhibitors of PKC isoforms, induce apoptosis and ceramide production through the activation of a neutral sphingomyelinase (Chmura et al., 1996a; Chmura et al., 1996b).

Ionizing radiation induces PKC and protein tyrosine kinase activities (Hallahan et al., 1990; Uckun et al., 1995). However, the specific kinases responsible for these activities and their substrates are not completely understood. PKC activation is functionally related to gene induction following exposure of mammalian cells to IR (Young et al., 1994; Kondratyev et al., 1996; Hallahan et al., 1995; Hallahan et al., 1994). The protein kinase C family of serine/threonine kinases is comprised of at least 13 related isoforms (Magnuson et al., 1994) with differing sensitivity to calcium and lipid activators. PKC activation is also reported to limit the production of ceramide from the hydrolysis of sphingomyelin and rescue cells from IR mediated apoptosis (Kolesnick et al., 1994; Haimovitz-Friedman et al., 1994).

Little information is available concerning the relationship between PKC inhibitors and the induction of programmed cell death in human tumor cells, and the results described in existing reports are inconsistent. For example, the potent, but nonspecific, PKC inhibitor staurosporine has been reported both to antagonize (Cotter et al., 1992) and to initiate apoptosis in HL-60 cells (Bertrand et al., 1993); similarly conflicting reports of the action of the inhibitor H7 have also appeared (Ojeda et al., 1990; Forbes et al., 1992). Detailed comparisons of the concentration-response relationships of different PKC inhibitors in the modulation of apoptosis are generally lacking. Jarvis et al. (1994) demonstrate that, while the effects of these agents are variable and highly dependent upon concentration, transient exposure of HL-60 cells to a subset of PKC inhibitors, in particular chelerythrine, unambiguously induces apoptotic DNA fragmentation and cell death in HL-60 cells and that acute (i.e., 6-h) exposure to chelerythrine is sufficient to induce apoptosis in the human myeloid leukemia cell line HL-60. In addition, in vitro treatment of certain cells with inhibitors of PKC and other serine-threonine kinases increases IR mediated killing through undefined mechanisms (Hallahan et al., 1992).

Recent investigations indicate that signaling events following cellular exposure to tumor necrosis factor alpha (TNFα), Fas ligand, IgM cross-linking, irradiation and other DNA damaging agents may trigger apoptosis via the hydrolysis of membrane sphingomyelin generating ceramide (Quintans et al., 1994; Nagata and Golstein, 1995; Dressier et al., 1992). Activation of protein kinase C by phorbol esters or growth factors opposes ceramide induced apoptosis and indirect evidence suggests that PKC activation may limit ceramide production (Fuks et al., 1994; Haimovitz-Friedman et al., 1994a; Haimovitz-Friedman et al., 1994b). One potential action of ceramide and its metabolite sphingosine is to prevent activation of specific PKC isoforms (Chmura et al., 1996b; Jones and Murray, 1995; Kolesnick, 1989; Ohta et al., 1994). Taken together, these studies suggest that PKC activation may oppose the actions of ceramide production in the apoptotic pathway.

Recent studies investigating mechanisms of radiation-mediated apoptosis demonstrate that the production of the lipid second messenger ceramide from sphingomyelin hydrolysis immediately following x-rays contributes to the apoptotic response (Kolesnick et al., 1994; Haimovitz-Friedman et al., 1994b; Verheij et al., 1996). Two forms of sphingomyelinase have been implicated in the generation of ceramide following x-rays. Involvement of the $Mg^{++}$ dependent neutral sphingomyelinase was first suggested as the source of ceramide generation at the membrane following ionizing radiation in endothelial cells (Haimovitz-Friedman et al., 1994). Recently Santana et al. demonstrated that tissues and cells from acidic sphingomyelinase knockout mice are more resistant to apoptosis following ionizing radiation (Santana et al., 1996). This study implicated acidic sphingomyelinase as a component of the apoptotic response in some tissues.

Much of the signaling interaction of PKC isoforms within tumor cells remains to be elucidated. It is clear that PKC pathways play a key role in the control of apoptosis by tumor cells. It is also evident that these pathways are altered in radioresistant tumor cells which results in an increased difficulty in treating these types of tumors. There is a present need to develop new and improved treatments which overcome the resistance to apoptosis of radioresistant tumors.

SUMMARY OF THE INVENTION

The invention provides a method for inhibiting growth of a tumor cell comprising contacting the tumor cell with chelerythrine and contacting the tumor cell with ionizing radiation, wherein the dose of the chelerythrine, when combined with the dose of ionizing radiation, is effective to inhibit growth of the tumor cell.

In one embodiment of the invention the tumor cell is contacted with chelerythrine prior to contacting it with the ionizing radiation. In another embodiment of the invention the tumor cell is contacted with ionizing radiation prior to contacting it with chelerythrine. In still another embodiment of the invention the chelerythrine and the ionizing radiation are contacted with the tumor cell simultaneously.

The invention provides that the dose of chelerythrine is about 0.5 mg/kg to about 10 mg/kg, and more preferrably the dose of chelerythrine is about 1 mg/kg to about 4 mg/kg.

The invention further provides that the ionizing radiation is selected from the group consisting of γ-irradiation, x-irradiation, microwave irradiation and ultraviolet irradiation wherein the total dose of ionizing radiation is about 1 Gy to about 80 Gy, but more preferably the total dose of ionizing radiation is about 70 Gy. The total dose of ionizing radiation is preferably administered in a series of aliquots.

In one aspect of the invention chelerythrine is contacted with the tumor cell at least twice. In another aspect of the invention ionizing radiation is contacted with the tumor cell at least twice.

In one embodiment of the invention the tumor cell is selected from the group consisting of a skin cancer cell, a prostate cancer cell, a lung cancer cell, a brain cancer cell, a breast cancer cell, an ovarian cancer cell, a cervical cancer cell, a liver cancer cell, a pancreatic cancer cell, a colon cancer cell, a stomach cancer cell and a leukemia cell. In another embodiment of the invention the tumor cell is a human tumor cell. In a further embodiment of the invention the human tumor cell is located in a human patient.

In another aspect of the invention the chelerythrine is administered systemically. In a particular aspect of the invention the chelerythrine is administered locally to a tumor mass containing the tumor cell. In still another aspect of the invention the chelerythrine is administered directly to a tumor mass containing the tumor cell. In a particular aspect of the invention the chelerythrine is administered to a resected tumor bed containing the tumor cell.

In another embodiment the invention provides that the ionizing radiation is administered to the entire patient. In a further embodiment the invention provides that the ionizing radiation is administered locally to a tumor mass containing the tumor cell.

The invention also provides a method of inducing apoptosis in a tumor cell comprising contacting the tumor cell with chelerythrine and contacting the tumor cell with ionizing radiation, wherein the dose of the chelerythrine, when combined with the dose of ionizing radiation, is effective to induce apoptosis in the tumor cell.

The invention further provides a method of killing a tumor cell comprising contacting the tumor cell with chelerythrine and contacting the tumor cell with ionizing radiation, wherein the dose of the chelerythrine, when combined with the dose of ionizing radiation, is effective to kill the tumor cell.

The invention further provides a method of treating cancer in a human patient comprising administering chelerythrine to the human patient and administering ionizing radiation to the human patient, wherein the dose of the chelerythrine, when combined with the dose of ionizing radiation, is effective to treat the cancer.

In one embodiment of the invention the cancer is selected from the group consisting of skin cancer, prostate cancer, lung cancer, brain cancer, breast cancer, ovarian cancer, cervical cancer, liver cancer, pancreatic cancer, colon cancer, stomach cancer and leukemia.

The invention further provides a method of potentiating the effect of ionizing radiation on a tumor cell comprising contacting the tumor cell with chelerythrine and then contacting the tumor cell with ionizing radiation.

As defined herein, treatment of a cancer, tumor, tumor cell, cancer cell, tissue derived from a tumor or cancerous tissue refers to any improvement over the untreated state which includes, but is not limited to, stabilization, remission, regression, shrinkage or decreased volume of the cancer, tumor, tissue or cell.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

In FIG. 3A, M1=5%; FIG. 3B, M1=22%; FIG. 3C, M1=73%; FIG. 3D, M1=16%; FIG. 3E, M1=24%.

FIG. 10A-1, FIG. 10A-2, FIG. 10A-3, FIG. 10A-4, FIG. 10A-5 and FIG. 10A-6. WEHI-231 OE cells were relatively apoptosis resistant compared to the JM cells yet remain sensitive to ceramide induced apoptosis. Terminal transferase and FACS analysis of WEHI-231 JM and OE cells 24 hours following treatment (+/–) with 10 Gy at the indicated time points. Cells were analyzed via flow cytometry (FACS) on a FACScan (Becton-Dickson) using Lysis II software with FL2 and FSH compensation set to 50% and 25% respectively. Abscissa: Number of Cells; Ordinate: log fluorescence of DNA fragmentation. R2 contains the apoptotic cells as scored against the positive control F15-12 cells and is represented as a smoothed contoured plot. The estimated percentage of apoptotic cells gated in R2 is shown (%) and is based on the original cell counting data.

FIG. 11A-1, FIG. 11A-2, and FIG. 11A-3. Exogenous ceramide can sensitize WEHI-231 OE cells to radiation mediated apoptosis. C2-ceramide (Cer) was added to $3 \times 10^5$ WEHI-231 OE cells 30 minutes prior to treatment with 8 Gy. Apoptosis was quantitated using propidium iodide staining and FACS analysis. Percent apoptotic cells are shown in gate R2 twenty-four hours following irradiation.

DESCRIPTION OF ILLUSTRATIVE EMBODIMENTS

Figure 1:
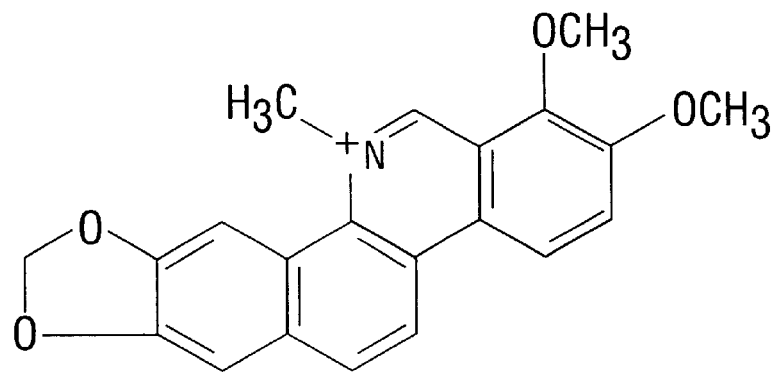
FIG. 1. Chemical structure of chelerythrine.

The present invention demonstrates that chelerythrine chloride decreases the apoptotic threshold in tumor cells, especially radioresistant cells, following IR. The induction of apoptosis by the combination of chelerythrine and IR is preceded by activation of both neutral and acidic sphingomyelinases. Surprisingly, this induction of apoptosis by the combination of chelerythrine and IR treatment occurs at doses much lower than would be expected based on conventional technology and treatments.

The combination treatment of tumor cells with IR and chelerythrine increases apoptosis and is dependent on activation of the caspases. These data are consistent with recent reports demonstrating that IR and ceramide induce apoptosis through the activation of CPP32 and other caspases (Kufe, 1996). Chelerythrine chloride enhances ionizing radiation induced apoptosis by targeting common components of the cell death pathway required for apoptosis and overcome resistance to radiation induced apoptosis in vitro and in vivo.

The observed divisional or mitotic linked death following IR at low chelerythrine concentrations contributes to tumor volume reduction in vivo. The increase in mitotic death following the combined radiation and chelerythrine treatment represents a non-apoptotic and therefore non-overlapping mechanism of tumor cell killing. The present invention demonstrates an increase in tumor cell destruction compared to surrounding normal tissue and indicates that chelerythrine combined with IR is a clinically useful tool for enhancing the lethal effects of ionizing radiation in resistant tumor cell populations.

A. Combination of Low Doses of Chelerythrine and Irradiation

Tumor cell resistance to DNA damaging agents represents a major problem in clinical oncology. One goal of current cancer research is to find ways to improve the efficacy of chemo- and radiotherapy. In the context of the present invention, it is contemplated that combination of chemotherapy with a PKC inhibitor, preferably chelerythrine or chelerythrine chloride, with radiation therapy can be used for therapeutic intervention. A surprising and unexpected result of the present invention is that the combination of chelerythrine and radiation allows for the use of lower doses of each composition in order to achieve a higher level of tumor growth reduction than would be predicted based upon current conventional radiation and chemotherapies. Thus toxic and other adverse effects which radiation causes to healthy cells that must be exposed to the radiation during treatment can be reduced by using the present invention.

Herein, it is understood that treatment with chelerythrine is preferentially with chelerythrine chloride.

To inhibit or even kill cells, such as malignant or metastatic cells, using the methods and compositions of the present invention, one would generally contact a "target" cell with a PKC inhibitor, such as chelerythrine, and low-dose ionizing radiation. These compositions would be provided in a combined amount effective to inhibit proliferation, or restore apoptotic function or even kill the cell. This process may involve contacting the cells with chelerythrine and irradiation simultaneously or with chelerythrine then irradiation or with irradiation and then chelerythrine. The cells may be contacted with a single composition or pharmacological formulation of chelerythrine, or with two or more distinct compositions or formulations of chelerythrine.

Irradiation sources include waves that induce DNA damage such as, γ-irradiation, X-rays, UV-irradiation, microwaves, electronic emissions, and the like. In treating cancer according to the invention, one would contact the tumor cells with radiation by irradiating the localized tumor site with DNA damaging radiation such as X-rays, UV-light, γ-rays or even microwaves.

It is envisioned that the regional delivery of chelerythrine to patients with cancers will be a very efficient method for delivering a therapeutically effective amount of the compound to counteract the clinical disease. Similarly, the radiotherapy will be directed to a particular affected region of the subject's body. Alternatively, systemic delivery of either chelerythrine, irradiation or both is appropriate in certain circumstances, for example, where extensive metastasis has occurred.

B. Chelerythrine, a Benzophenanthridine Alkaloid

The benzophenanthridine alkaloid chelerythrine (1,2-dimethoxy-12-methyl[1,3]benzodioxolo[5,6-c]phenanthridinium; $C_{21}H_{18}NO_4$), also known as toddaline, is extractable either in pure form or as a mixture with other benzophenanthridine alkaloids from Chelidonium majus L., Zanthoxylum simulans, Sanguinaria candensis (or bloodroot), Macleaya cordata, Carydali sevctocozii, Carydali ledebouni, Chelidonium majusm and other members of Papaveracaceae. The major alkaloid in Zanthoxylum simulans, is chelerythrine with smaller quantities of dihydro- and oxy-chelerythrine, N-acetylanomine, skimmianine, fagarine, sitosterol and sesamine. Gray et al, (1980) describes the extraction and identification of chelerythrine and other constituents from Zanthoxylum simulans.

Other benzo-c-phenanthridine alkaloids which may be present in the plants with chelerythrine include sanguinarine, sanguirubine, sanguilutine, homochelidonene, chelirubine and protopine among others. Pure chelerythrine is also available, although rarely, from some chemical supply houses. Semi-purified forms of benzo-c-phenanthridine alkaloids are commercially available, and these are generally referred to as sanguinarine nitrate and sanguinarine sulfate. These "salts" are the salts of the mixed alkaloids of the plant Sanguinaria and mainly comprise sanguinarine, chelerythrine, and protopine.

While few references can be found in the literature regarding the usage of any of the pure benzo-c-phenanthridine alkaloids, plants containing such compounds have been used for medical purposes for quite some time for a wide variety of ailments. For example, U.S. Pat. No. 209,331, discloses the use of bloodroot, zinc chloride, and kerosene oil in equal proportions for treating open sores. U.S. Pat. No. 433,257 describes a salve of pulverized bloodroot, armenian bole, powdered rosin, lard, and Stockholm tar for use in the treatment of piles, and U.S. Pat. No. 2,344,830, discloses the use of a mixture of zinc chloride, stibnite, and bloodroot, to fix and outline diseased tissue for excision by surgery. Some of the patents describing the use of sanguinaria extracts as antimicrobial agents are U.S. Pat. Nos. 4,145,412; 4,406,881; and 4,376,115. Chelerythrine has also been used for the treatment of peridontal disease, U.S. Pat. No. 5,324,520, and in the treatment of thrombosis, U.S. Pat. No. 5,137,912. Benzo-c-phenanthridine alkaloids have also been shown to have some antifungal and antiprotozoan properties, alleviate the mild anemia lingering after an acute illness and the mild anemia associated with rheumatoid arthritis.

In China, people use the berries of Zanthoxylum simulans to flavor pork. The long and widespread use of this extract in China shows that the extract is safe for human consumption. The extract has an absence of any noticable side effects and lack of irritation to the gastrointestinal tract. Moreover, the extract has been found to help alleviate the gastrointestinal irritations which may occur through the use of the anti-inflammatory agents when coadministered.

Chelerythrine specifically inhibits protein kinase C (PKC) in a concentration-dependent manner and strongly inhibits platelet aggregation induced by strong aggregation inducers, such as arachidonic acid and collagen. Its chemical structure is shown in FIG. 1.

Inhibitors of PKC can interact with the substrate binding site (ATP or protein) or with the regulatory domain where activation occurs (diacylglycerol or phorbol ester binding site). Chelerythrine interacts directing with the catalytic domain of PKC. It is one of the most potent inhibitors of PKC identified and does not inhibit any other protein kinases investigated. Chelerythrine shows potent cytotoxic effects against L-1210 tumor cells with an IC50 value of 0.053 $\mu$M by inhibiting cell growth and differentiation (Herbert et al., 1990).

Chelerythrine exhibits biphasic concentration-response relationships such that DNA fragmentation declines and eventually subsides as drug levels are increased beyond maximally effective concentrations (Jarvis et al, 1994). Reductions in DNA damage are not associated with restoration of cellular viability, however, indicating that other lethal events proceeded unimpaired.

Under the conditions described by Herbert et al. (1990) the $IC_{50}$ value (concentration causing a 50% inhibition) for chelerythrine is 0.66 $\mu$M in rats. Basal activity of the enzyme (the activity in the absence of $Ca^{++}$, phosphatidylserine and dioleine) was not affected. In the present invention, the $LD_{50}$ (dose causing a 50% mortality) was 20 mg/kg intraperitoneal (IP) in mice.

An effective dose of chelerythrine is highly dependent upon the route of administration used and the size and species of animal being treated. In general, orally delivered doses can be higher than injected doses for any given individual. In the present invention, an effective dose is a dose that can induce apoptosis in a treated cell. Particularly desirable cells to treat include tumor and cancer cells and especially radio-resistant tumor or cancer cells. An exemplary effective dose range is equivalent to about 0.5–10 mg/kg (IP) in a mouse and more preferably 1–4 mg/kg (IP) in a mouse.

C. Ionizing Radiation

Ionizing radiation causes DNA damage and cell killing, generally proportional to the dose rate. Ionizing radiation has been postulated to induce multiple biological effects by direct interaction with DNA or through the formation of free radical species leading to DNA damage (Hall, 1988). These effects include gene mutations, malignant transformation, and cell killing. Although ionizing radiation has been demonstrated to induce expression of certain DNA repair genes in some prokaryotic and lower eukaryotic cells, little is known about the effects of ionizing radiation on the regulation of mammalian gene expression (Borek, 1985). Several studies have described changes in the pattern of protein synthesis observed after irradiation of mammalian cells. For example, ionizing radiation treatment of human malignant melanoma cells is associated with induction of several unidentified proteins (Boothman, et al., 1989). Synthesis of cyclin and co-regulated polypeptides is suppressed by ionizing radiation in rat REF52 cells but not in oncogene-transformed REF52 cell lines (Lambert and Borek, 1988). Other studies have demonstrated that certain growth factors or cytokines may be involved in x-ray-induced DNA damage. In this regard, platelet-derived growth factor is released from endothelial cells after irradiation (Witte, et al., 1989).

In the present invention, the term "ionizing radiation" means radiation comprising particles or photons that have sufficient energy or can produce sufficient energy via nuclear interactions to produce ionization (gain or loss of electrons). An exemplary and preferred ionizing radiation is an x-radiation. Means for delivering x-radiation to a target tissue or cell are well known in the art. Also, the phrase "effective expression-inducing dose of ionizing radiation" means that dose of ionizing radiation needed to stimulate or turn on a "radiation responsive enhancer-promoter" that is one embodiment of the present invention.

1. Radiation Responsive Enhancer-promoters

A radiation responsive enhancer-promoter (as described in U.S. Pat. No. 5,571,797 and incorporated herein by reference) is a promoter whose transcription controlling function is affected by ionizing radiation. The enhancer-promoter region is used as a switch to selectively affect expression of a polypeptide encoded by that sequence. The regulation of specific polypeptide expression in a distinct target cell or tissue provides opportunities for therapeutic destruction, alteration or inactivation of that cell or tissue.

A promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit. Exemplary and preferred promoters are the TATA box, the CAAT box and GC-rich sequence elements.

Another type of discrete transcription regulatory sequence element is an enhancer. An enhancer provides specificity of time, location and expression level for a particular encoding region (e.g., gene). A major function of an enhancer is to increase the level of transcription of an encoding region in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. As used herein, a "radiation responsive enhancer-promoter" indicates an enhancer-promoter whose transcription controlling function is affected by ionizing radiation. Typically, upon exposure to an effective dose of ionizing radiation, a radiation responsive enhancer-promoter of the present invention stimulates or increases the rate of transcription of an encoding region controlled by that enhancer-promoter. An exemplary and preferred enhancer-promoter for use in a DNA molecule of the present invention is a CArG domain of an Egr-1 promoter, a promoter for tumor necrosis factor-alpha (TNF-$\alpha$) gene or a c-Jun promoter.

A radiation responsive enhancer-promoter is operatively linked to an encoding region that encodes at least one polypeptide. As used herein, the phrase "operatively linked" means that an enhancer-promoter is connected to an encoding region in such a way that the transcription of that encoding region is controlled and regulated by that enhancer-promoter. Means for operatively linking an enhancer-promoter to an encoding region are well known in the art. As is also well known in the art, the precise orientation and location relative to an encoding region whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at considerable distance from that site.

2. Dosage and Delivery of Ionizing Radiation

The amount of ionizing radiation needed in a given cell generally depends upon the nature of that cell. Typically, an effective expression-inducing dose is less than a dose of ionizing radiation that causes cell damage or death directly. Means for determining an effective amount of radiation are well known in the art. The amount of ionizing radiation needed in a given cell naturally depends upon the nature of that cell. As also used herein, the term "an effective dose" of ionizing radiation means a dose of ionizing radiation that produces an increase in cell damage or death when given in conjunction with a virus.

In a certain embodiments, an effective expression inducing amount is from about 1 to about 30 Gray (Gy) administered at a rate of from about 0.5 to about 4 Gy/minute. Even more preferably, an effective expression inducing amount of ionizing radiation is from about 1 Gy to about 80 Gy (total dose). In other embodiments, doses of about 1–9 Gy are used in single doses. An effective dose of ionizing radiation is from about 4.5 Gy to about 100 Gy, with a total of about 70 Gy (either singly or more preferably in multiple aliquot doses) being preferred. These dose ranges are well below the doses used in conventional radiation therapy and thereby reduce the deleterious side effects associated with higher doses of radiaton.

Any suitable means for delivering radiation to a tissue can be employed in the present invention in addition to external means. For example, radiation can be delivered by first providing a radiolabeled antibody that immunoreacts with an antigen of the tumor, followed by delivering an effective amount of the radiolabeled antibody to the tumor. In addition, radioisotopes may be used to deliver ionizing radiation to a tissue or cell.

Tumors that can be treated with the present invention include, but are not limited to, tumors of the brain (glioblastomas, medulloblastoma, astrocytoma, oligodendroglioma, ependymomas), lung, liver, spleen, kidney, lymph node, small intestine, pancreas, blood cells, colon, stomach, breast, endometrium, prostate, testicle, ovary, skin, head and neck, esophagus, bone marrow, blood or other tissue. The tumor may be distinguished as metastatic and non-metastatic. Various embodiments include tumor cells of the skin, muscle, facia, brain, prostate, breast, endometrium, lung, head & neck, pancreas, small intestine, blood cells, liver, testes, ovaries, colon, skin, stomach, esophagus, spleen, lymph node, bone marrow or kidney. Other embodiments include fluid samples such as peripheral blood, lymph fluid, ascites, serous fluid, pleural effusion, sputum, cerebrospinal fluid, lacrimal fluid, stool or urine.

D. Therapeutic Regimens

The treatment with chelerythrine may precede or follow irradiation by intervals ranging from seconds to weeks. In embodiments where chelerythrine and irradiation are applied separately to the cell, one would generally ensure that a significant period of time did not expire between the time of each delivery, such that the combination of the two would still be able to exert an advantageously combined effect on the cell. In such instances, it is contemplated that one would contact the cell with both agents within about 0.1 to 24 hours of each other and, more preferably, within about 1 to 4 hours of each other, with a delay time of only about 1 hour to about 2 hours being most preferred. In some situations, it is desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either chelerythrine or irradiation will be desired. Various combinations may be employed, where chelerythrine is "A" and irradiation is "B":

| | | | |
|---|---|---|---|
| A/B/B | B/A/A | A/A/B | |
| A/B/A | B/A/B | B/B/A | |
| B/B/B/A | B/B/A/B | B/A/B/A | B/A/A/B |
| A/A/B/B | A/B/A/B | A/B/B/A | B/B/A/A |
| A/A/A/B | B/A/A/A | A/B/A/A | |
| B/A/B/B | A/A/B/A | A/B/B/B | |

To achieve cell killing, both agents are delivered to a cell in a combined amount effective to kill the cell.

Dosage ranges for X-rays range from daily doses of 50 to 200 cGy for prolonged periods of time (6 to 8 weeks), to single doses of 2000 to 6000 cGy. Dosage ranges for radioisotopes vary widely, and depend on the half-life of the isotope, the strength and type of radiation emitted, and the uptake by the neoplastic cells.

E. Treatment Routes

Chelerythrine can be administered intravenously, intraarterially, intratumorally, parenterally or intraperitoneally. In the invention, the preferred routes of administration are directly intratumoral, injection of a resected tumor bed, intravenous (IV), intrarterial, and intraperitoneal (IP). Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Chelerythrine may also be orally administered, for example, with an inert diluent or with an assimilable edible carrier, or enclosed in hard or soft shell gelatin capsule, or compressed into tablets, or incorporated directly with the food of the diet. For oral therapeutic administration, the active compound may be incorporated with excipients and used in the form of ingestible tablets, buccal tables, troches, capsules, elixirs, suspensions, syrups, wafers, and the like. Such compositions and preparations should contain at least 0.1% of the active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

F. Screening and Monitoring Effectiveness of Therapy

It is contemplated that in the context of the present invention one may remove cells, either tumor, normal or both tumor and normal cells, from an individual in order to either monitor the progress of treatment or as a part of the treatment. It is expected that one may monitor the effectiveness of treatment by removing such cells and treating such cells with DAPI staining to determine the level of chromatin condensation, measuring the level of apoptosis, measuring the level of neutral sphingomyelinase production or other methods such as the following.

One particluar method for determining induction of apoptosis is terminal deoxynucleotidyl transferase mediated dUTP-biotin nick end labeling (TUNEL) assays, which measure the integrity of DNA (Gorczyca, 1993). This assay measures the fragmentation of DNA by monitoring the incorporation of labeled UTP into broken DNA strands by the enzyme terminal transferase. The incorporation can be monitored by electroscopy or by cell sorting methodologies (e.g., FACS).

G. Ex vivo Delivery

In the present invention, it is contemplated that systemic delivery of either or both chelerythrine and irradiation may be used. It is further contemplated that in practicing the claimed invention that one will wish to replace affected cells with healthy cells from the same patient. Ex vivo gene therapy refers to the isolation of cells from an animal or patient, the delivery of a nucleic acid into the cells in vitro, and then the return of the modified cells back into an animal or individual. This may involve the surgical removal of tissue/organs from an animal or patient or the primary culture of cells and tissues.

In particular, autologous bone marrow cell (BMC) transplantation is used as a salvage procedure in which blood or bone marrow is taken and stored prior to an intensification of radiation or chemotherapy. In preparing human mononuclear cells (MNC), an aliquot of marrow is layered into a receptacle such as a centrifuge tube. Initially, MNC may be obtained from a source of bone marrow, e.g., tibiae, femora, spine, ribs, hips, sternum, as well as the humeri, radi, ulna, tibiae, and fibulae. Additionally, these cells also can be obtained from cord blood, peripheral blood, or cytokine-mobilized peripheral blood. Other sources of human hematopoietic stem cells include embryonic yolk sac, fetal liver, fetal and adult spleen, and blood. The marrow layer is centrifuged to produce a pellet of red cells at the bottom of the tube, a clear layer of media, an interface layer which contains the MNC and a plasma medium layer on top. The interface layer may then be removed using, for example, suction. Centrifugation of this layer at 1000 g ultimately yields a MNC pellet. This pellet may then be resuspended in a suitable buffer for cell sorting by FACS. The isolated MNC are cloned in vitro to expand the of immunologically active cells. The expanded, therapeutically active cells are then provided to the patient to obtain a therapeutic effect.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods

Drugs and Reagents

Chelerythrine [$IC_{50}$ (PKC)=0.66 $\mu$M, $IC_{50}$ (PKA)=170 $\mu$M] and Calphostin C [$IC_{50}$ (PKC)=0.50 nM, $IC_{50}$ (PKA) 50 $\mu$M] show high specificity for the PKC family of enzymes (Sigma). These inhibitors are at least 30 fold more specific at blocking PKC activity as opposed to the relatively non-selective yet widely used agents staurosporin and H7. They do not appear to inhibit other kinases such as the cyclic-AMP kinase (PKA) at concentrations used for the inventors' studies.(Kobayashi et al., 1989b; Herbert et al., 1990). 7-amino-actinomycin D, ATP, phosphate buffered saline (PBS), sphingosine-1-phosphate, DL-threo-dihydrosphingosine and propidium iodide were purchased from Sigma Chemical Corp., St. Louis, Mo. C2-ceramide and n-oleoylethanolamine were purchased from Matreya Chemicals, Pa. Reagents for the terminal transferase assay were purchased from Boehringer-Mannheim Biochemicals, Indianapolis, Ind. Thin-layer chromatography plates were purchased from Whatman (10 cm×10 cm LHP-K TLC plate). Autoradiography film was from Dupont. [$^3$H] palmitic acid (60 Ci/mmol), [$^{14}$C] sphingomyelin (60 Ci/mmol), and [γ-$^{32}$P] ATP were purchased from DuPont NEN. All solvents were HPLC grade. Chelerythrine was dissolved in sterile water for the in vitro experiments or PBS for the intratumoral injections.

Cell Culture

The SQ20B human head and neck squamous cell carcinoma line was grown in DMEM supplemented with 25% F5-12, 20% fetal bovine serum(Gibco/BRL, Grand Island, N.Y.), and 1% penicillin-streptomycin at 5% $CO_2$ following standard procedures as described in (Chmura et al., 1996a; 1996b) except for the modifications described below. WEHI-231 JM were grown at a density of 3–6×10$^5$ cells/ml in RPMI 1640 culture medium, 1% penicillin-streptomycin, 10% heat inactivated fetal calf serum (Gibco/BRL, Grand Island, N.Y.), and 5×10$^{-5}$ M β-mercaptoethanol (Sigma) in 5% $CO_2$.

Viability Assay via Propidium Iodide Exclusion

Cells, 2.5–3.5×10$^5$, were cultured in 24-well tissue culture plates for all experiments following standard procedures as previously described (Chmura et al., 1996a; 1996b). Cells were treated with varying concentrations of chelerythrine, incubated for 30 minutes at 37° C. and then irradiated. Radiation for all samples was delivered using a $^{60}$Co-irradiator (Gammacell 220, Atomic Energy of Canada) at a dose rate of 2.0 Gy/sec. After the indicated time points, cells were harvested, washed once in PBS, and resuspended in PBS containing 50 ml of 100 mg/ml propidium iodide. Live cells do not uptake propidium iodide, but dead cells do. Cells undergoing apoptosis also shrink in size. Cells were analyzed via flow cytometry (FACS) following standard procedures as described in (Chmura et al., 1996a; 1996b) on a FACScan (Becton-Dickson) using Lysis II software.

DAPI Staining for Nuclear Visualization

Cells, 5×10$^5$, were centrifuged at 1000 rpm and resuspended in approximately 100 μl cell culture media. The cell suspension was then mixed with 100 μl of DAPI (4',6-iamidino-2-phenylindole, Sigma D9542, 1 μg/ml in PBT (PBS+1% Triton X-100)). One drop of this mixture was placed on a microslide with a coverslip. The cells were viewed by fluorescence microscopy using an Olympus BX-40 microscope with a 100 Watt Mercury lamp, a 16 or 40 X Fluorite objective, N.A. 0.75, (Leco #1-UB527) and a UV filter cube (ex 330–385 nm, em 420 nm, wide band pass, Leco #U-M536). Images were photographed using an Optronics cooled low-light video camera (Leco #DEI-470TB) to which was attached a 2X coupler (Leco #HR200-CMT). The image was saved to a digital file at 72 dpi.

DNA Laddering Assay

DNA degradation was assessed as previously described (Gottschalk et al., 1993; 1994). Briefly, following treatment in 100 mm plates or 24 well plates, cells were collected and lysed in 0.5 ml lysis buffer (0.6% SDS+10 mM EDTA, pH 7.0). NaCl was added to a final concentration of 1M, mixed by inversion, incubated for 12 hours at 4° C. and then spun at 14,000 g for 30 minutes. Samples were treated with chloroform (1:1) and precipitated in ethanol prior to electrophoresis in a 3% agarose gel and visualized with ethidium bromide.

Colony Formation Assay

Exponentially growing SQ20B cultures were trypsinized using 0.05% trypsin+0.02% EDTA. Cells (100 to 50,000) were plated in 100 mm tissue culture dishes. Chelerythrine or C2-ceramide was added 4 hours after plating and irradiated for 30 minutes after the addition of chelerythrine or C2-ceramide. The cells were irradiated using a GE Maxitron 250 x-ray generator operating at 250 kV and 26 mA with a dose rate of 114 cGy/min. After 12 days the cells were fixed and stained with crystal violet following standard procedures (Chmura et al., 1996a; 1996b). Colonies of >50 cells were scored as survivors.

Ceramide and DAG Quantification by DAG Kinase Reaction

Quantitation of ceramide by diacylglycerol kinase was similar to that described by Dressler and Kolesnick (1990). After irradiation, lipids were extracted and resuspended by bath sonication in 20 μl of 7.5% n-octyl-β-D-glucopyranoside, 5 mM cardiolipin, 1 mM DETAPAC. Seventy μl of a reaction mix was added to give a final concentration of 0.05M imidazole/HCl pH 6.6, 0.05M NaCl, 12.5 mM $MgCl_2$, 1 mM EGTA and DAG kinase at a concentration of 0.7 U/ml. The reaction was started by the addition of 10 μl of [γ-$^{32}$P]ATP (1.0 μCi/tube) in 5 mM ATP and incubated at room temperature for 30 min and stopped by the extraction of lipids with 450 μl of $CHCl_3$:$CH_3OH$ (1:2) and 20 μl of 1% $HClO_4$. The monophase was mixed and after 10 min., 150 μl $CHCl_3$ and 150 μl of 1% $HClO_4$ were added and the tubes vortexed and centrifuged at 5000 g for 5 min. The lower organic phase was washed twice with 1% $HClO_4$ and then dried in a Speed Vac Apparatus. The phosphorylation products, ceramide-1-phosphate and phosphatidic acid (fom DAG) were resolved on a 10 cm×10 cm LH P-K TLC plate (Whatman). Data was calculated as pmoles of ceramide/10$^6$ cells by scintillation counting. In Example 6, data (mean +/− SD) represent at least 4 independent studies in which *p<002 compared with unirradiated controls.

Labeling, Extraction, and Analysis of [3H] Palmitic Acid Labeled Lipids

Cells were prelabeled with [$^3$H] palmitate (10 μCi/ml) for 24 hours to isotopic equilibrium in 15 ml glass tubes to minimize changes in cellular ceramide and sphingomyelin due to handling and changing of media (Borchardt et al., 1994). Following treatment of cells with chelerythrine, total lipids were extracted via a modified Folch method. Briefly, 1 ml of MeOH: 2N HCL (100:6, v/v) was used to resuspend the cell pellet. Chloroform (2 ml) and water (0.6 ml) were added to each tube, vortexed 3 times, and centrifuged for 20 minutes at 1000×g producing a bi-layer. Equal amount of the organic phase was taken from each tube, dried, and reconstituted with 30 μl of chloroform:methanol (95:5). An aliquot (10 μl) was streaked on a 10 cm×10 cm LHP-K TLC plate (Whatman), previously run in a wash solvent of $CHCl_3$:$CH_3OH$:$H_2O$(60:40:10, v/v). Sphingolipids were resolved in $CHCl_3$:$MeOH$:$CH_3COOH$:$H_2O$ (32.5:12.5:4.4:2.25), iodine-stained, sprayed with En$^3$Hance (DuPont) and autoradiographed. Autoradiographs were quantitated using an Epson 1200 c 30 bit scanner and NIH Image software (public domain program developed at the NIH and available from the Internet via FTP from zippy.nimh.nih.gov). Both counting and density analysis provided similar results.

Assay for Neutral and Acidic Sphingomyelinase Activity

The mixed micellar sphingomyelinase assay using [$^{14}$]C labeled sphingomyelin was performed as described (Wiegmann et al., 1994) with minor modifications as described herein. Exponentially growing cells 2×10$^7$ were treated, collected, and lysed in 200 μl of neutral buffer (20 mM Hepes, pH 7.4; 10 mM $MgCl_2$, 2 mM EDTA, 5 mM DTT, 100 mM $Na_3VO_4$, 100 mM $NaMO_4$, 10 mM b-glycerolphosphate, 750 μM ATP, 1 mM PMSF, Leupeptin, Pepstatin, 2% Triton X-100) or an acid buffer (pH=5.5, 2% Triton X-100, 1 mM PMSF, Leupeptin, Pepstatin). After incubation for 5 minutes at 4° C., cells were homogenized by sonication and cell debris were removed by low speed centrifugation (800×g). The protein concentration was measured using the BioRad protein assay system (BioRad). Protein (50 μg) was incubated for 2 hours at 37° C. in a buffer (1 ml final volume) containing 20 mM HEPES, 1 mM MgCl$_2$, and 0.9 μl [N-methyl-$^{14}$C sphingomyelin]. The reaction was linear at this protein concentration. Phosphorylcholine was then extracted with 800 ml of chloroform-:methanol (2:1 v/v) and 250 ml H$_2$0. Radioactive phosphorylcholine was measured by scintillation counting. Data is expressed as a percent of control for both the acidic and neutral sphingomyelinases. In Example 6, data (mean +/− SEM) were derived from 4 independent studies with 2 or more determinants in which p<0.04 for neutral sphingomyelinase activity in WEHI-231 JM cells (Student's t-test) compared with unirradiated controls.

Growth of Human Tumor Xenografts

SQ-20B (1–5×10$^6$) tumor cells were injected into the right hind limbs of nude mice (Fredrick Cancer Research Institute). Xenografts were grown for 2–3 weeks to a mean tumor volume of 300 mm$^2$. At day 0, initial tumor volume was determined by direct measurement with calipers. During treatment tumor volumes were measured with calipers twice weekly and represented as percent of original tumor volume. Tumor volumes were calculated by the formula (a×b×c/2) which was derived from that for an ellipsoid (d3/6). Tumor cure was defined as regression to a volume of <10% of original size since, at this volume, it is impossible to differentiate residual tumor from scar tissue. Xenografts were injected with 2 mg/kg chelerythrine chloride on days 0, 3, 7 and 10. Irradiated mice were immobilized in lucite chambers and the entire body was shielded with lead except for the tumor bearing hind limb 14. Tumors were irradiated (5 Gy/day, 4 days/week) to a total dose of 50 Gy using a Maxitron generator (1.88 Gy/min.). Tumors were treated with radiation alone, chelerythrine alone, and buffer or chelerythrine combined with radiation. Data were calculated as the percent of original (day 0) tumor volume and graphed as fractional tumor volume±SEM.

Histology of SQ-20B Xenografts

Tumors were injected once or twice (day 0 and day 4) with chelerythrine, chelerythrine and 20 Gy (5 Gy/Day) or 20 Gy alone and excised on day 7, fixed in 10% neutral buffered formalin. Tumors were then trimmed and processed in a Tissue Tek II Tissue Processor. Tissues were embedded in paraffin, sectioned and stained with hematoxylin and eosin or with 100 ml of DAPI (4',6-iamidino-2-phenylindole, Sigma D9542, 1 μg/ml in PBT (PBS+1% Triton X-100)), followed by examination for apoptosis and necrosis by light microscopy.

Isolation of Nuclei

WEHI-231 JM cells (2×10$^7$) were pelleted and resuspended in extraction buffer (20 mM Hepes pH 7.4; 10 mM MgCl$_2$; 2 mM EDTA; 5 mM DTT; 100 mM Na$_3$VO$_4$; 100 mM NaMO$_4$; 10 mM β-glycerolphosphate; 750 μM ATP; 1 mM PMSF, 10 μM Leupeptin, 10 μM Pepstatin; 2% Triton X). Cells were incubated on ice for 5 minutes and then disrupted with 15 strokes of a dounce homogenizer. Nuclei, prepared fresh before each study, were washed twice with RPMI spinning at 2000 RPM in a microcentrifuge and resuspended in media containing RPMI and 5×10$^{-5}$ M β-mercaptoethanol. Radiation for all samples was delivered using a $^{60}$Co-irradiator (Gammacell 220, Atomic Energy of Canada) at a dose rate of 2.0 Gy/sec.

Selection of OE Variants

WEHI-231 JM cells (1×10$^7$) were treated with two successive treatments of 100 μM and 125 μM N-oleoylethanolamine (Matreya), a potent inhibitor of ceramidase (Coroneos et al., 1995; Ambrosini et al., 1994). Cells were grown in media containing n-oleoylethanolamine for 96 hours. Serial dilutions isolated individual resistant cells and were expanded after each selection. Every two weeks cells were re-selected with 125 μM n-oleoethanolamine. The resulting cell lines, named WEHI-231 OE, are 3-fold more resistant to apoptosis when treated with 75 μM of the inhibitor yet the cells possess similar growth kinetics compared with the parental line.

Assays for Apoptosis and Cell Viability

The TdT assay was performed as previously described (Chmura, 1996). Irradiated (10 Gy) and serum starved FL5-12 generated the apoptotic region designated as R2. Cells were analyzed via flow cytometry on a FACScan (Becton-Dickson) using Lysis II software with FL2 and FSH compensation set to 50% and 25% respectively.

To detect DNA fragmentation, cells were collected and lysed in 0.5 ml lysis buffer (0.6% SDS+10 mM EDTA, pH 7.0). NaCl was added to 1M and mixed by inversion and left for 12 hours in 4° C. and spun at 14,000 g for 30 minutes. Samples were chloroform and ethanol (1:1) precipitated and run in a 3% agarose gel stained with ethidium bromide.

For viability staining, 2.5–3.5×10$^5$ cells were treated with varying concentrations of C2-ceramide, irradiation, or both. After the indicated time points, cells were harvested, washed once in phosphate buffered saline (PBS), resuspended in PBS containing 50 μl of 100 μg/ml propidium iodide, and analyzed by flow-cytometry (FACS).

EXAMPLE 1

Chelerythrine Chloride Potentiates IR-induced Decrease in Clonogenic Survival

SQ20-B, a human laryngeal carcinoma cell line, is radiation-resistant (D$_0$=2.3 Gy) when compared to other human cell lines (Nagasawa et al., 1994; Brachman et al., 1993). Mutations within exon 5 of p53 in SQ20-B result in a lack of cell cycle G1 arrest and no increase in p53 protein following IR-exposure (Brachman et al., 1993).

Figure 2:
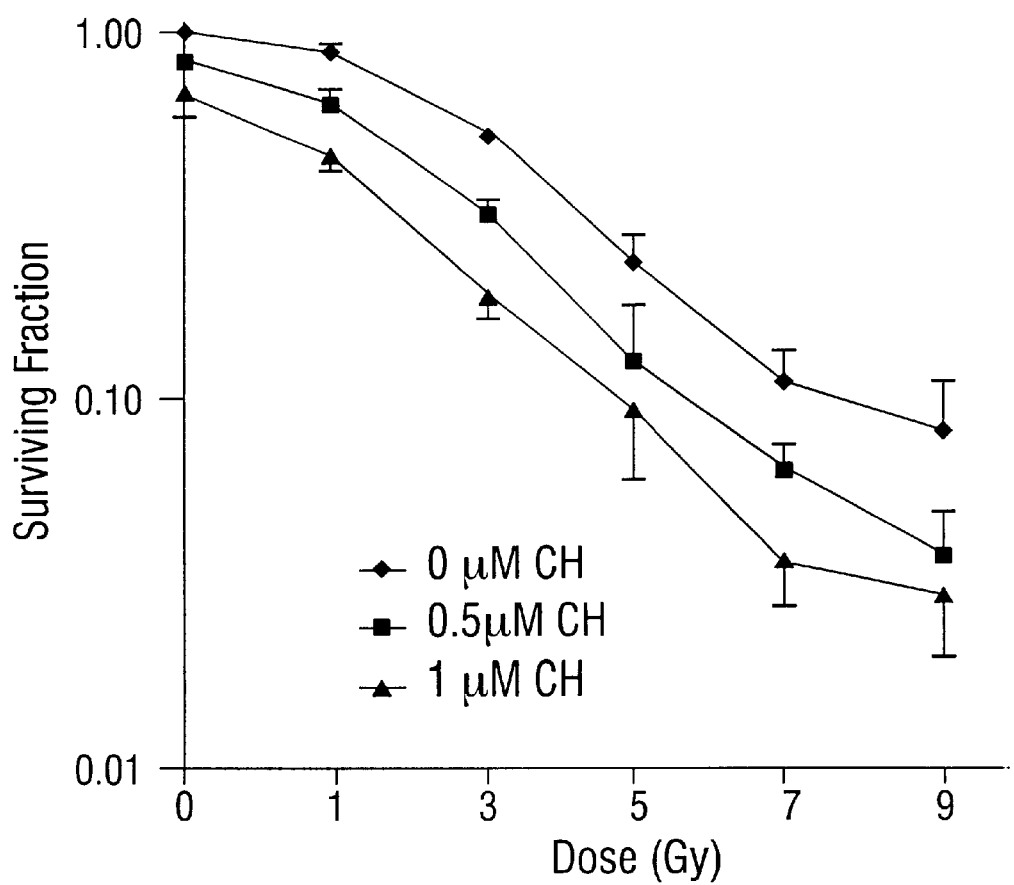
FIG. 2. Chelerythrine chloride enhanced IR-mediated cell killing through divisional death. Clonogenic survival was measured following exposure to increasing concentrations of chelerythrine and ionizing radiation. Cells were plated at cell numbers between about 500 cells/plate and about 2000 cells/plate and treated with 0 $\mu M$, 0.5 $\mu M$, or 1.0 $\mu M$ chelerythrine chloride for 30 minutes prior to irradiation. After 2 weeks the colonies were scored for survival if they were composed of more than 50 cells. Results represent the mean of three individual experiments with duplicate or triplicate determinants. Error bars represent +/− the standard error of the means (SEM).
Figure 3A:
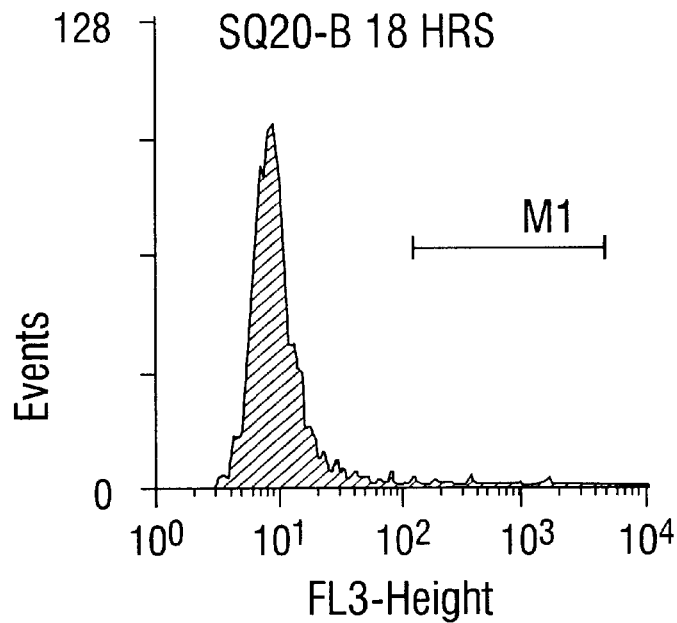
FIGS. 3A–3E. Propidium iodide staining of SQ20-B cells treated with chelerythrine demonstrates that zVAD-fmk inhibits programmed cell death. M1 defines the % of apoptotic cells as defined by (a) propidium iodide uptake of 1 log or more fluorescence and (b) a decrease in cell size of 50% or more. FL3-Height indicated the uptake of propidium by the cell.
Figure 3B:
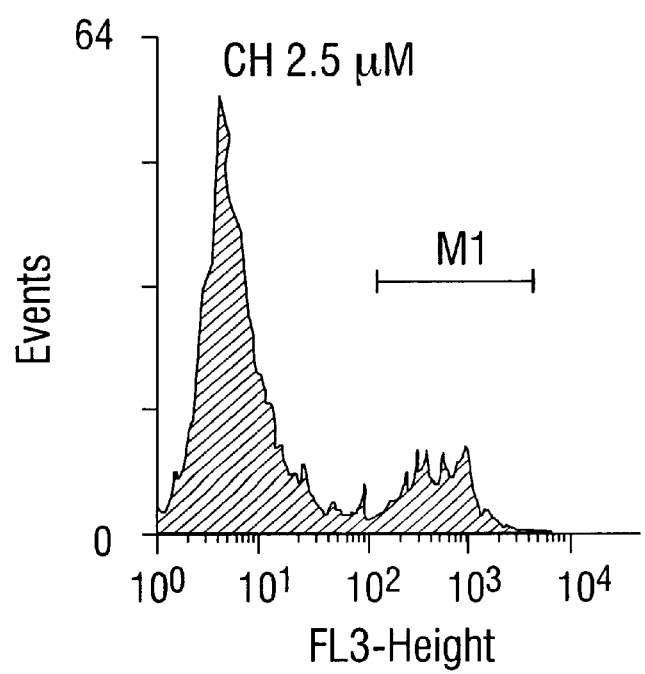
Figure 3C:
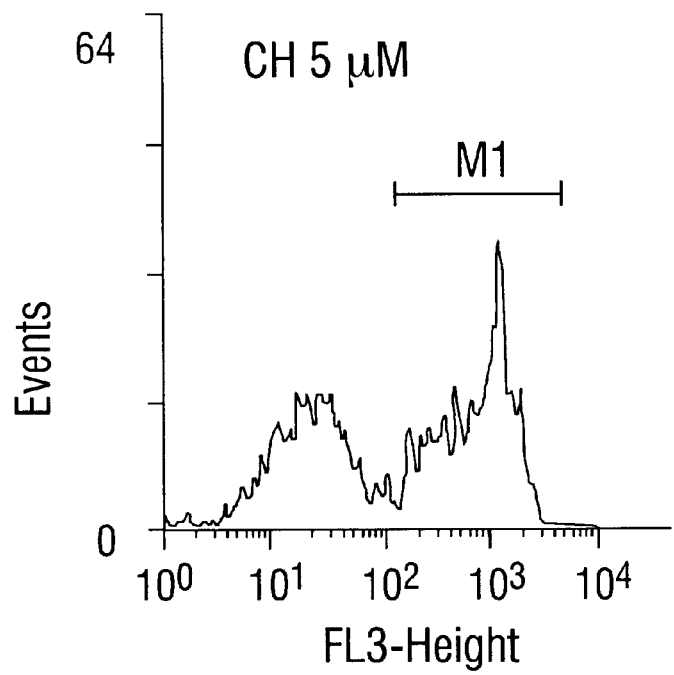
Figure 3D:
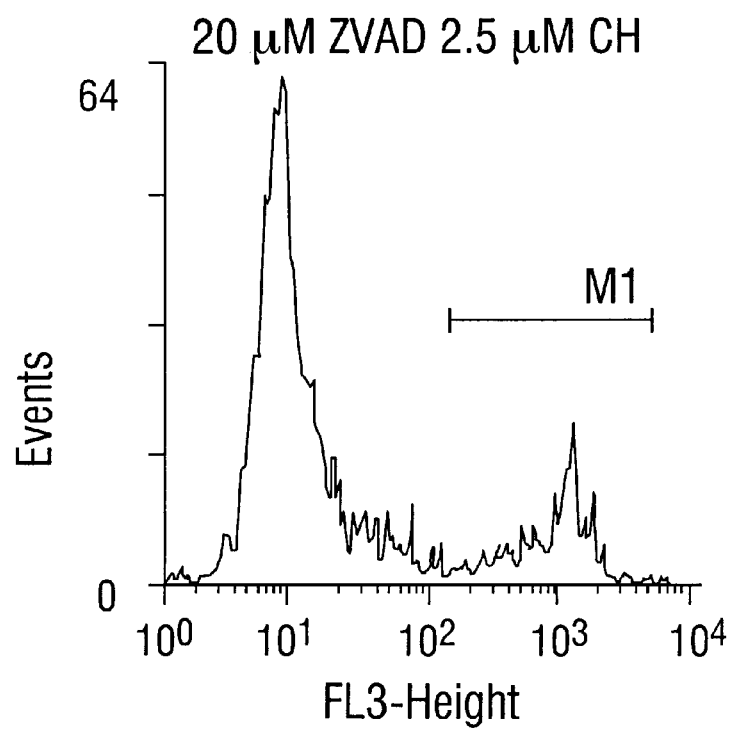
Figure 3E:
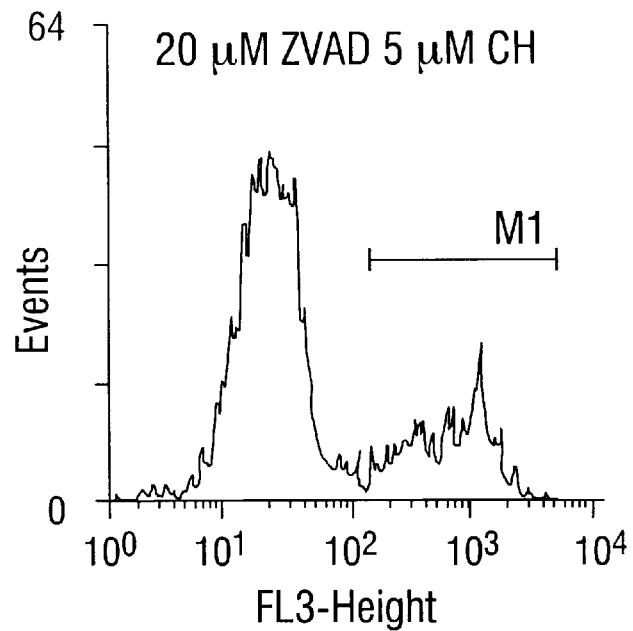

Clonogenic survival was measured following increasing concentrations of chelerythrine chloride alone (0.5–1.5 μM), IR alone (1–9 Gy), or the combined treatment of cells with chelerythrine and IR. The addition of chelerythrine to exponentially growing SQ20-B cells decreased clonogenic survival in a concentration-dependent manner (FIG. 2). At a concentration of 500 nM, chelerythrine decreased cell survival to about 80% of untreated control cells (about 20% cell death). The combined treatment of cells with 500 nM of chelerythrine 30 minutes prior to treatment with 3 Gy of radiation decreased cell survival to about 30% of untreated cells (about 70% cell death). Cell death was increased by chelerythrine across the dose range delivered (1–9 Gy) and resulted in both decreased clonogenic survival and abortive colony formation (FIG. 2). Cell shrinkage and nuclear condensation, characteristic of apoptosis, were not observed at these concentrations of chelerythrine and IR. These data demonstrate that nanomolar concentrations of chelerythrine enhance IR-mediated cell death by mechanisms independent of apoptosis.

EXAMPLE 2

SQ20-B Cells Lack an Apoptotic Response to IR

There was no detectable chromatin condensation or cytoplasmic blebbing at 72 hours after exposure of SQ-20B cells to 20 Gy IR, and the cells appeared similar to untreated controls. By contrast, 10 μM chelerythrine induced chromatin condensation, cytoplasmic blebbing, and internucleusomal DNA fragmentation 12 hours after exposure to chelerythrine. These data demonstrate that, while SQ-20B retains the capacity to undergo apoptosis, IR alone is insufficient to initiate the apoptotic response.

To determine if the induction of apoptosis by chelerythrine involved activation of caspases, the irreversible zVAD-fmk peptide inhibitor of these proteases was used. The addition of zVAD-fmk, blocked chelerythrine induced apoptosis. These findings indicate that chelerythrine initiates apoptosis through activation of CPP32 or a related caspase (FIGS. 3A–3E).

EXAMPLE 3

Figure 4:
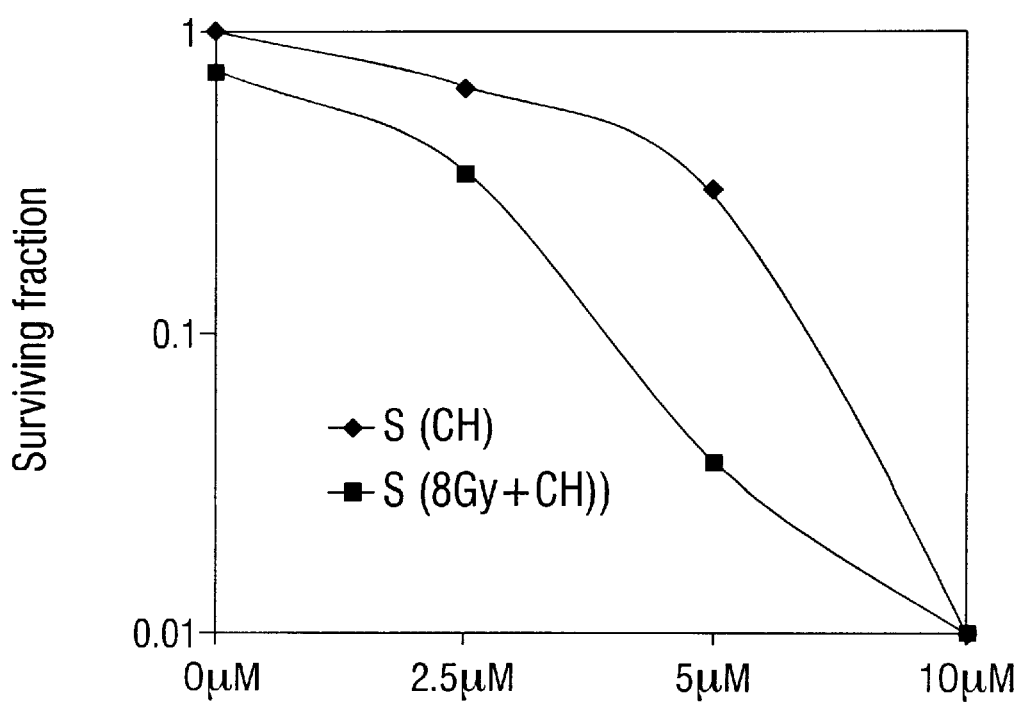
FIG. 4. Viability of SQ20B cells 72 hours after treatment with irradiation and chelerythrine in vitro.

Chelerythrine Enhances IR Induced Apoptosis Following Sphingomyelinase Activation As assayed by propidium iodide exclusion and FACS analysis, treatment of SQ-20B cells with x-ray (8 Gy) and increasing amounts of chelerythrine decreased cell viability by 25% of control cells at 48 hours (FIG. 4). The decrease in cell viability represents the maximal number of cells which may have died an apoptotic death at the first post-IR cell division following IR. By contrast, 8 Gy IR decreased clonogenic survival by 90%. These findings suggest that the major mechanism of IR induced cell death is divisional (necrotic). The combination of 2.5 μM chelerythrine and 8 Gy induced morphological changes consistent with apoptosis similar to those observed with 10 μM chelerythrine alone and decreased cell survival by 85% (FIG. 4). The combined effects of IR and chelerythrine showed greater than additive killing with concentrations of chelerythrine above 2.5 μM. These results indicate that the marked increase in cell death within 48 hours following the combined treatment of cells with chelerythrine and IR results from a decrease in the apoptotic threshold of SQ20-B cells to IR.

The protease inhibitor zVAD-fmk (20 μM) inhibited apoptosis following the combined treatment of cells with IR and chelerythrine (2.5 μM) similar to that observed with chelerythrine (10 μM) alone. Previous studies suggested that non-specific PKC inhibitors shorten the G2/M phase of the cell cycle and thus increase cell killing by ionizing radiation (Thompson and Fields, 1996). In the present invention, treatment of SQ20-B cells with 0.5–1 μM chelerythrine failed to shorten the G2/M phase observed in irradiated cells. Concentrations of chelerythrine alone which induced apoptosis (5 μM), however, also induced an arrest in the G2/M phase of the cell cycle (Thompson and Fields, 1996). These results demonstrate that chelerythrine increases divisional death at concentrations below the threshold which induces caspase dependent apoptosis.

Figure 5A:
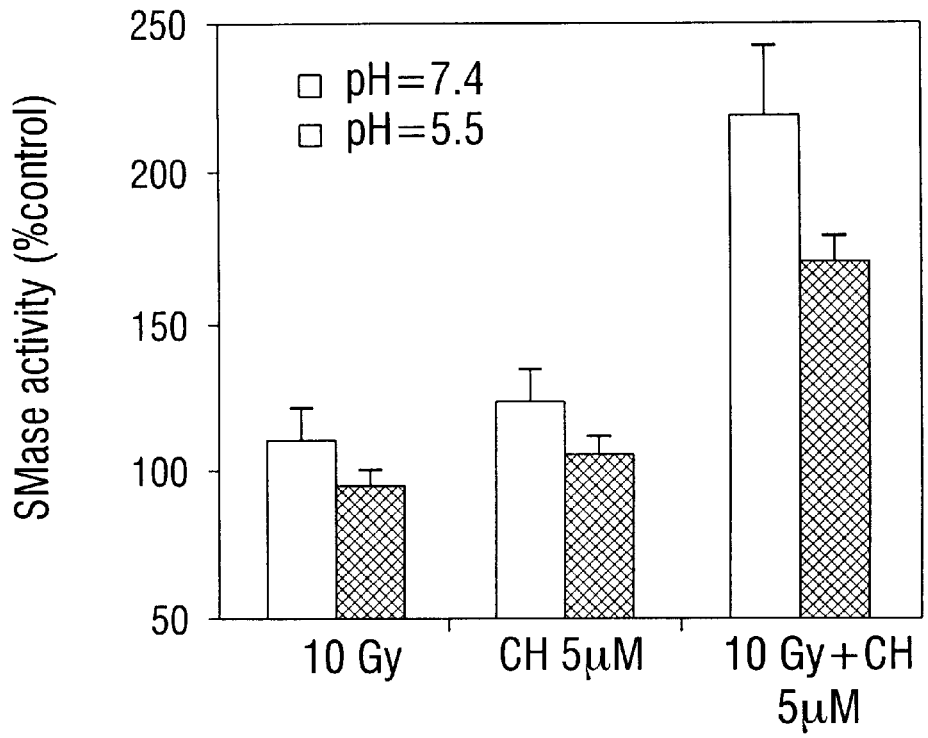
FIG. 5A. Neutral and acidic sphingomyelinase activity were enhanced following the concomitant treatment of chelerythrine and ionizing radiation. The mixed micellar assay for sphingomyelinase activity was used to quantitate increased enzymatic activity. Radiation alone failed to show increased sphingomyelinase activation over control. Treatment of cells with chelerythrine increased sphingomyelinase activity to about 212% and about 179% over control for neutral and acidic sphingomyelinase, respectively. The combined treatment of cells with x-rays and chelerythrine increased both neutral and acidic sphingomyelinase activities to an average of about 200% and about 170% of control, respectively.
Figure 5B:
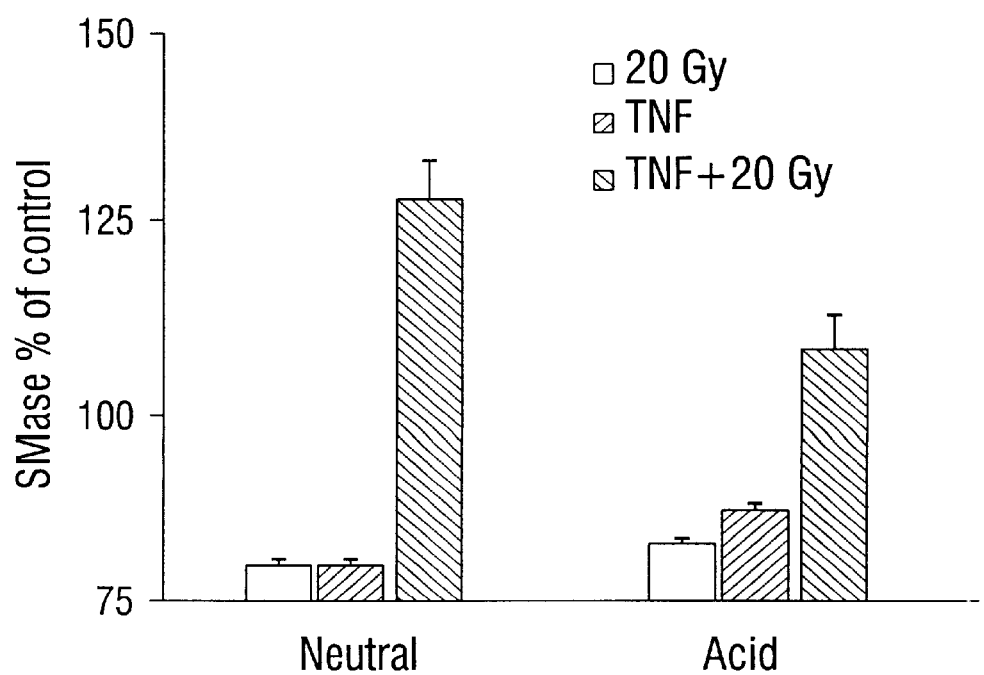
FIG. 5B. Effects of irradiation (20 Gy), tumor necrosis factor (TNFα) and the combination of irradiation (20 Gy) and TNFα(5 ng) on the activation of neutral and acidic sphingomyelinase in the SQ20B model as measured with the sphingomyelinase assay 5 minutes after irradiation.

Previous work has suggested that chelerythrine enhances apoptosis, in part, through activation of sphingomyelinases (Chmura et al., 1996b). Neutral and acidic sphingomyelinase activities were measured in irradiated SQ-20B cells using a mixed micellar assay. Exposure of SQ-20B cells to 10 Gy failed to alter sphingomyelinase activity within 30 minutes of treatment (FIG. 5A). SQ20B cells were pre-treated with 5 μM chelerythrine for 30 minutes and then exposed to 10 Gy. Consistent with findings in other cell lines (Chmura et al., 1996a; Chmura et al., 1996b), neutral and acidic sphingomyelinase increased to about 200% ($p<0.03$) and about 170% ($p<0.005$) of untreated control, respectively, within 5 minutes of IR exposure (FIG. 5B).

Figure 5C:
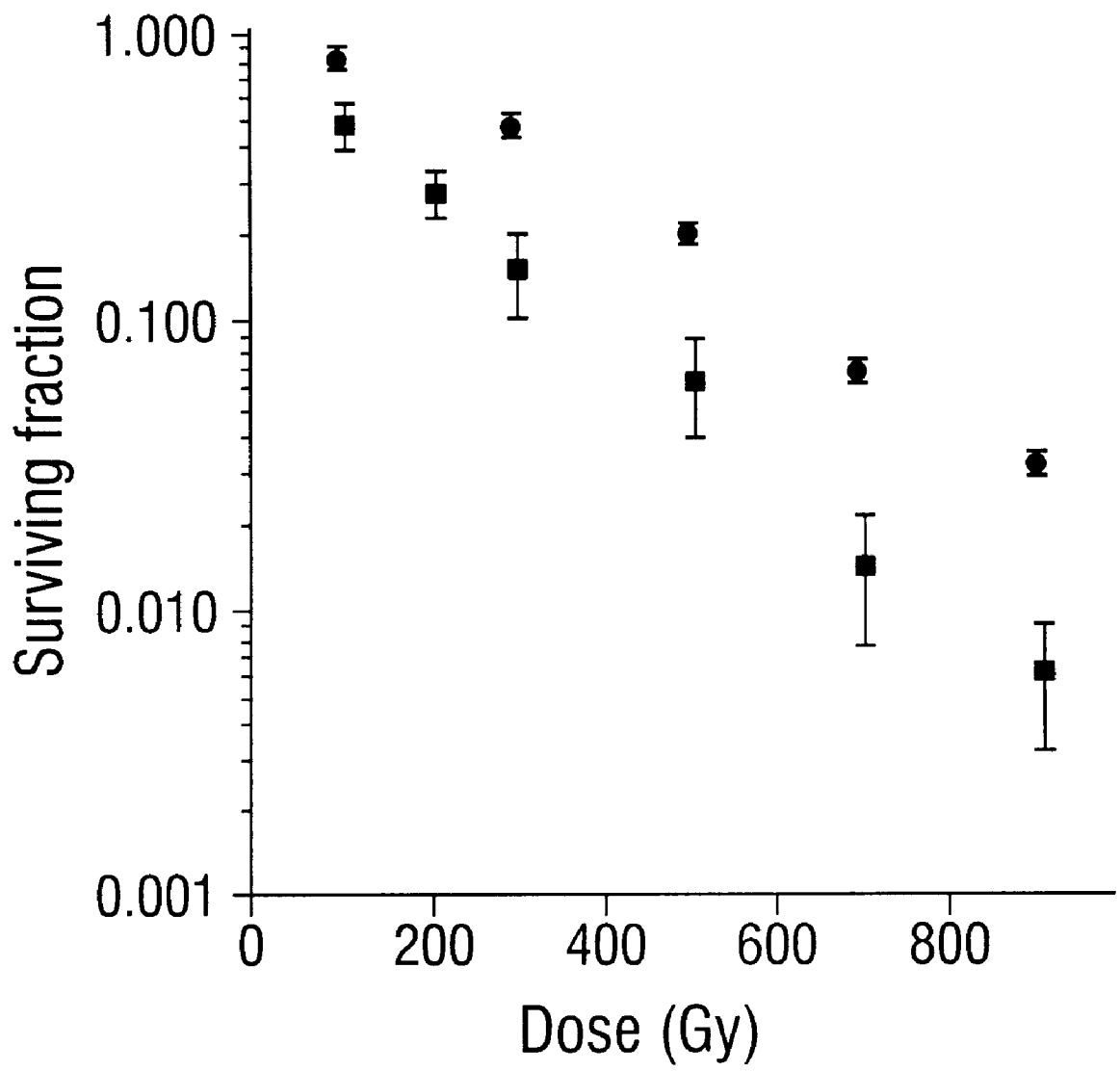
FIG. 5C. The addition of ceramide to irradiated cultures decreased clonogenic survival. Closed circles represent radiation alone; closed squares represenet addition of 20 μM C2-Ceramide 30 minutes prior to x-ray.

Ceramide production and a coordinate decrease in sphingomyelin mass followed the increase in sphingomyelinase activity. Significantly, exogenous ceramide added 30 minutes prior to irradiation enhanced IR induced cell killing (FIG. 5C). These studies demonstrate that the combination of chelerythrine and IR increases sphingomyelinase activity before the appearance of apoptosis.

EXAMPLE 4

Chelerythrine Enhanced Apoptosis and Cell Killing by X-rays in vivo

Figure 6:
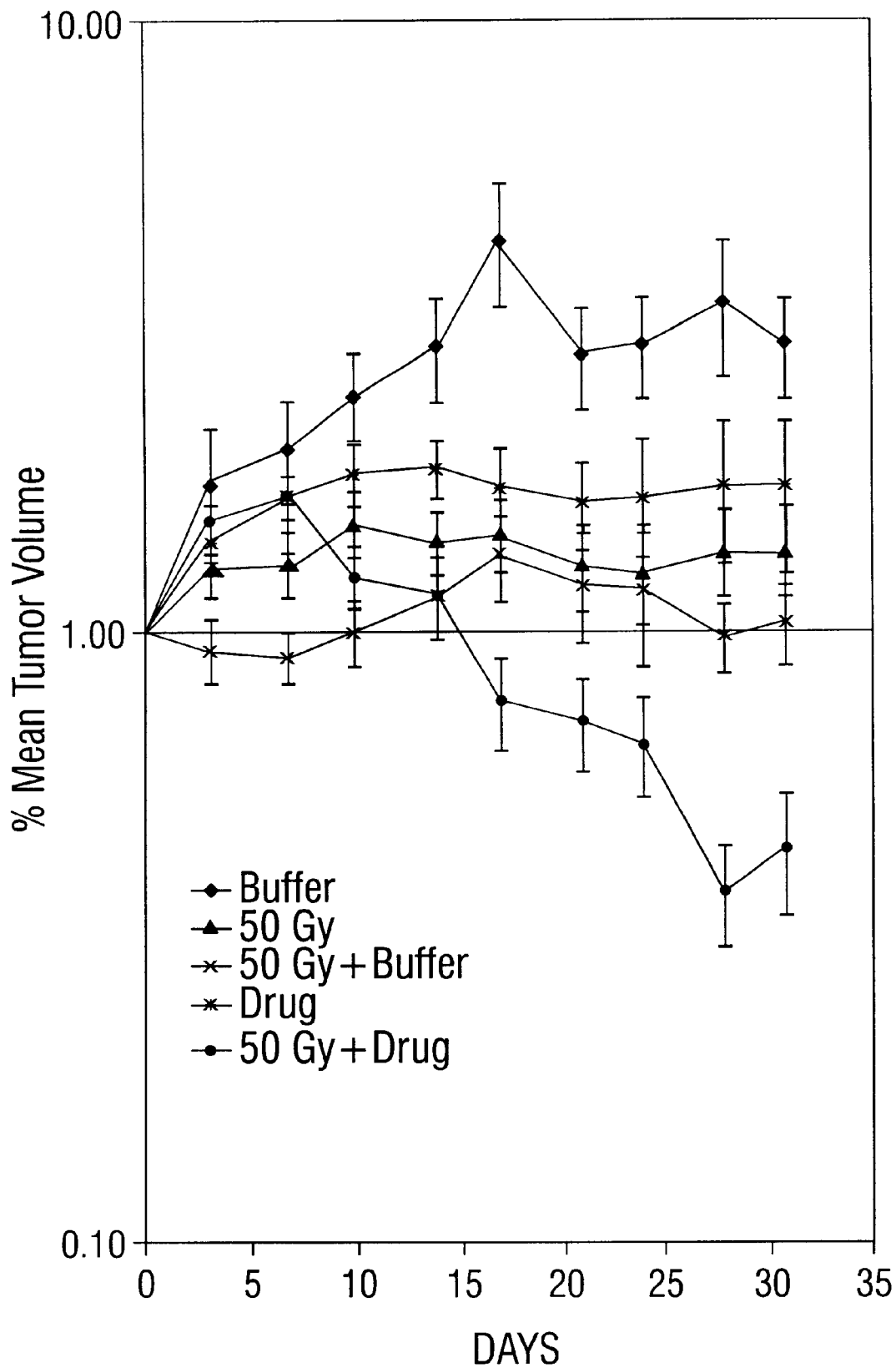
FIG. 6. The SQ-20B xenograft system was used to assess the therapeutic efficacy of the combined treatment modality over 30 days. Forty animals (n=40) were treated in each group and the % mean tumor growth was determined for all animals. Calipers were used to measure tumor growth. The combination of a non-lethal dose of chelerythrine (drug) with 50 Gy IR (5 Gy fractions over 2 weeks) decreased tumor volume and increased cell killing over either treatment alone (P<0.001 Mann-Whitney Rank Sum Test).

The increase in cell killing by chelerythrine chloride following IR in vivo enhanced tumor cell killing of SQ-20B xenografts in nude mice. Tumors with initial mean volumes between 305–895 mm$^3$ were injected with 2 mg/kg chelerythrine chloride ($LD_{50}$ 25 mg/kg IP) four times during treatment on days 0, 3, 7, and 10. Radiation was delivered at 5 Gy/day, 4 days per week, for a total of 50 Gy. The animals in all treatment groups appeared healthy throughout the study. As shown in FIG. 6, compiled data for 4 separate experiments demonstrate that chelerythrine chloride (n=43) or radiation alone (n=28) initially inhibited tumor regrowth compared with buffer injected controls (n=26). However, by day 30 following treatment tumor regrowth reached 138% and 174% of the original volume in radiation and chelerythrine alone treatment groups respectively.

In the combined treatment group at day 31, 20/41 animals showed tumor regression to less than 10% of their original volume. In contrast, 1/16 of the radiation+buffer and 13/43 of the chelerythrine only treated animals regressed to less than 10% of the initial tumor volume. Thus the combined effect of chelerythrine and IR is greater than the additive effects of either treatment alone. Histological analysis of tumors revealed large areas of increased tumor necrosis over x-irradiation (XRT) or chelerythrine treatment alone as early as 4 days following combined treatment. Representative sections of non-necrotic areas of tumors were stained with DAPI to detect nuclear changes of apoptosis. Tumor sections were taken at day 7 following treatment with 2 injections of chelerythrine alone, 20 Gy alone, 1 injection of chelerythrine and 20 Gy, or 2 treatments with chelerythrine and 20 Gy. Nuclei from non-necrotic areas of tumors treated with radiation alone appeared rounded and contained a smooth heterachromatin appearance. Few apoptotic nuclei as defined by chromatin margination and nuclear shrinkage could be detected in these areas. Nuclei from chelerythrine treated tumors appeared similar to that from radiation treated.

In contrast to either radiation or chelerythrine treatment alone, nuclei from tumors treated with a single dose of chelerythrine and 20 Gy fractionated 5 Gy/day for 4 days appeared shrunken and fragmented within the non-necrotic tumor sections. No areas of viable tissue could be found in the tumors treated with two treatments of chelerythrine and x-ray. While treatment of tumors with IR induced a typical inflammatory response and necrosis in the underlying epidermis and muscle tissue, the combined treatment of tumors with x-ray and chelerythrine did not increase this response suggesting that the enhanced cell killing by chelerythrine was limited to the tumor bed. These results demonstrate that while ionizing radiation fails to induce apoptosis in vivo, chelerythrine enhances radiation induced cell killing through the induction of apoptosis within days of treatment and that the underlying and surrounding normal tissues are relatively spared from the effects of this treatment.

EXAMPLE 5

PKC Inhibition Induces Apoptosis and Ceramide Production

In order to understand the potential interactions between PKC activity, ceramide production, and apoptosis, two inhibitors of PKC, chelerythrine chloride and calphostin C were employed. Chelerythrine chloride and calphostin C compete for the conserved catalytic sites and regulatory domains of PKC respectively and are potent and specific inhibitors of the PKC isoforms ($\alpha,\beta,\delta,\epsilon$) found in WEHI-231 cells (Chmura et al., 1996a; Rotenberg et al., 1995; Herbert et al., 1990; Haggerty and Monroe, 1994). PKC inhibition with chelerythrine or calphostin C induced apoptosis. Furthermore treatment of cells with chelerythrine or calphostin C enhanced ceramide production following the activation of a neutral sphingomyelinase indicating that PKC and the lipid second messenger ceramide play opposing roles in determining survival following diverse cellular signals.

Chelerythrine and Calphostin C Induced Apoptosis

Twenty-four hours following the addition of chelerythrine (10 $\mu$M) or calphostin C (250 nM) to WEHI-231 growing in complete media, propidium iodide FACS analysis demonstrated greater than 90% cell death. Gel electrophoresis of low molecular weight DNA and DAPI fluorescent staining revealed DNA laddering and nuclear condensation. Taken together, these results established that WEHI-231 undergo apoptosis following treatment with inhibitors of PKC.

Chelerythrine and calphostin C were found to act in synergy with exogenous ceramide analogs to induce apoptosis (Chmura et al., 1996a). This finding is consistent with previous reports demonstrating that phorbol esters limit ceramide toxicity in WEHI-231 and other cell lines (Haimovitz-Friedman et al., 1994a; Gottschalk and Quintans, 1995; Obeid et al., 1993). Since activation of PKC may limit ceramide production (Fuks et al., 1994; Haimovitz-Friedman et al., 1994a; Haimovitz-Friedman et al., 1994b), the effects of decreased PKC activity on ceramide accumulation were examined.

Ceramide Production is Due to the Activation of a Neutral Sphingomyelinase

Figure 7A:
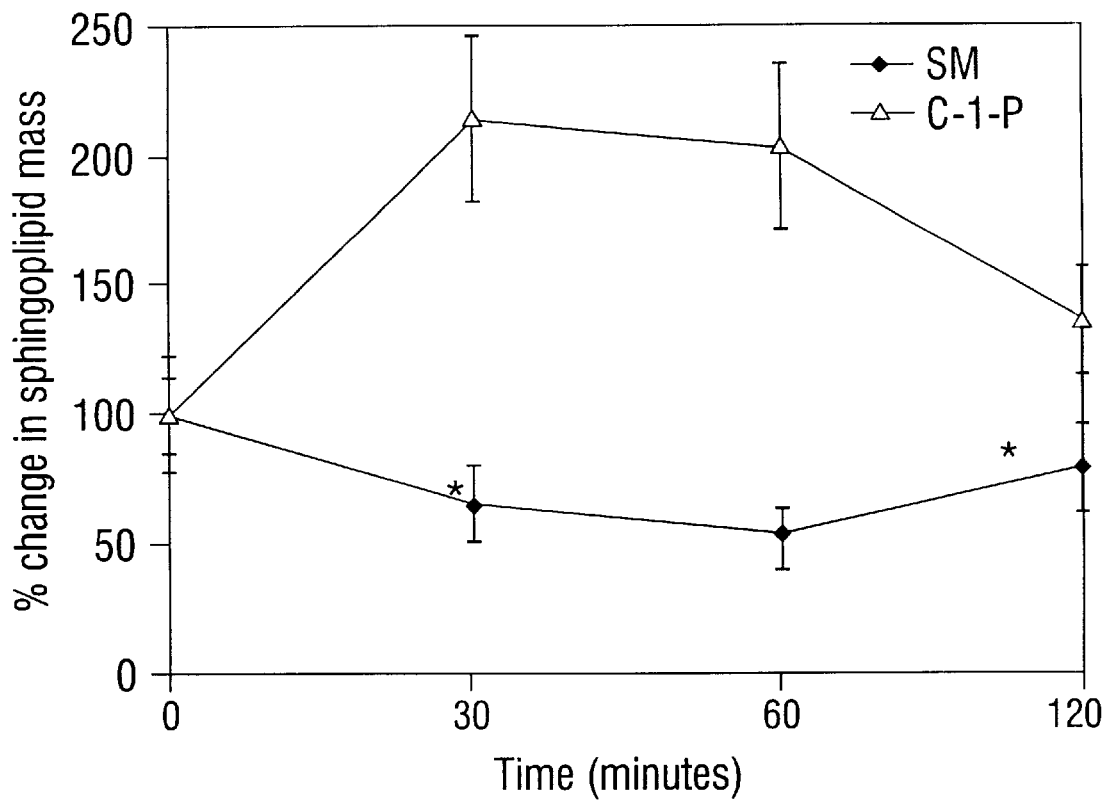
FIG. 7A. Inhibition of PKC causes an increase in ceramide production through the activation of a neutral sphingomyelinase and decreases in sphingomyelin levels. Ceramide production was quantitated using the DAG kinase assay for WEHI-231 JM cells and total lipid extraction was used to assay sphingomyelin mass. Following addition of 10 μM chelerythrine, cells were lysed at the appropriate time points as described herein. Each data point represents the average percentage change in ceramide or sphingomyelin generation from baseline derived from at least 8 independent studies for all time points with the exception of those marked with * (n=4). Standard deviations depicted by error bars. No change in viability or cell size was detectable at the 2 hour time point as assayed by propidium iodide exclusion and FACS.

In order to test whether PKC inhibition alters ceramide production, the DAG kinase assay was used to quantify intracellular ceramide following chelerythrine and calphostin C treatment (Dressler and Kolesnick, 1990; Preiss et al., 1986). FIG. 7A depicts the time course of ceramide production following the addition of 10 $\mu$M chelerythrine to exponentially growing cell cultures. Approximately 30 minutes following the addition of chelerythrine, ceramide generation increased 100% over baseline and returned to a near pretreatment level within hours. Thus PKC inhibition induced ceramide accumulation within the first hour following treatment with the inhibitor.

Figure 7B:
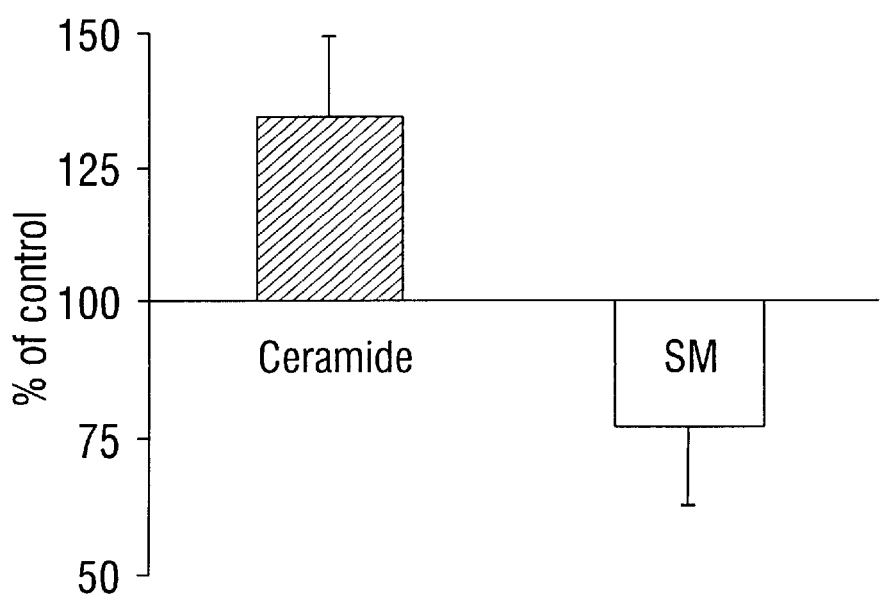
FIG. 7B. Calphostin C induced cerarnide production and decreased sphingomyelin levels. Ceramide production and sphingomyelin mass was quantitated identical to that for chelerythrine. Cells were lysed 2 hours following the addition of 250 nM calphostin C. The average percentage change in ceramide and sphingomyelin generation from baseline is derived from at least three independent studies. Standard deviations are depicted by error bars.

In order to investigate whether the increase in ceramide occurred through the hydrolysis of its respective precursors or from new lipid synthesis, sphingomyelin levels were examined in WEHI-231 following treatment with chelerythrine. Cells (4×10$^6$) were labeled with [$^3$H]-palmitate (10 $\mu$Ci/ml) for 24 hours, total lipids extracted, and separated using thin-layer chromatography as previously detailed (Quintans et al., 1994). FIG. 7A shows that sphingomyelin mass decreased concurrently with the increase in ceramide and reached its lowest levels 60 minutes (about 55% of control) following treatment with the inhibitor. As shown in FIG. 7B, calphostin C had similar effects on ceramide production and sphingomyelin levels. Thus inhibition of PKC caused not only increased intracellular ceramide, but a concurrent decrease in sphingomyelin, suggesting that ceramide is produced through the hydrolysis of its precursor by a sphingomyelinase.

Figure 7C:
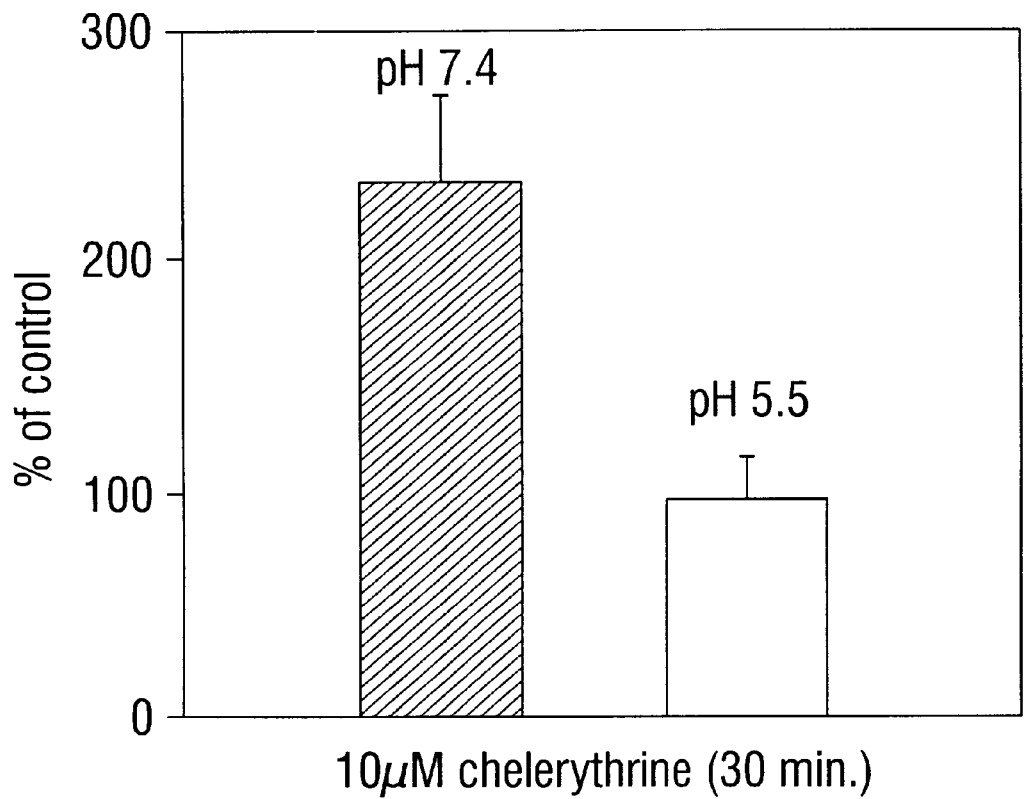
FIG. 7C. Graph of neutral and acidic sphingomyelinase activity normalized to percent of control. Cells ($2 \times 10^7$) were treated with chelerythrine for 30 minutes prior to being assayed for neutral or acidic sphingomyelinase activity. Error bars represent +/– SEM from 4 individual studies with duplicate determinants.

To confirm that ceramide accumulation was due to increased sphingomyelinase activity, a mixed micellar assay was used to quantitate in-vitro enzyme activity. Chelerythrine was used preferentially for these studies due to its greater solubility and light independent activity. FIG. 7C illustrates that neutral, but not acidic, sphingomyelinase activity increased to 235% (+/−38 SD) of control within 30 minutes of exposure to chelerythrine suggesting that a majority of the ceramide accumulation resulted from the hydrolysis of sphingomyelin. Heat inactivated chelerythrine had no effect on cell viability nor sphingomyelinase activation. Furthermore, chelerythrine studied in the absence of cellular preparations did not induce hydrolysis of labeled sphingomyelin demonstrating that increased cellular sphingomyelinase activity was responsible for sphingomyelin hydrolysis.

Figure 8A:
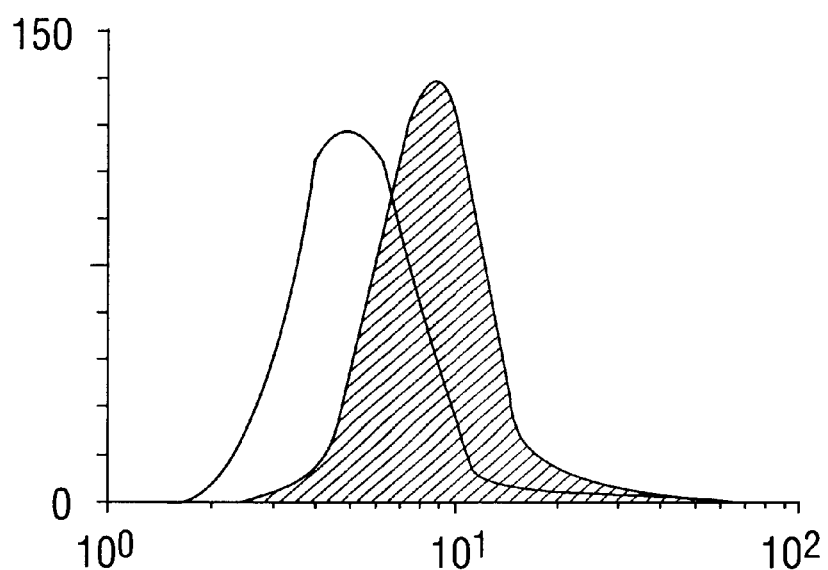
FIGS. 8A–8C. Exogenous ceramide and PKC inhibition induce oxidative changes in WEHI-231 cells. WEHI-231 cells ($1 \times 10^6$) were treated with anti-IgM antibodies for 2 hours (FIG. 8A), 30 μM exogenous ceramide for 15 minutes (FIG. 8B) or 10 μM chelerythrine for 15 minutes (FIG. 8C). The reactive oxygen species in the cells was then measured using dichlorodihydrofluorescein (DCHF-DA) and quantitated using FACS analysis. Histogram analysis of fluorescence is plotted as LOG function. The gray area represents the control cells while the overlaid line plot demonstrates the treated cells.
Figure 8B:
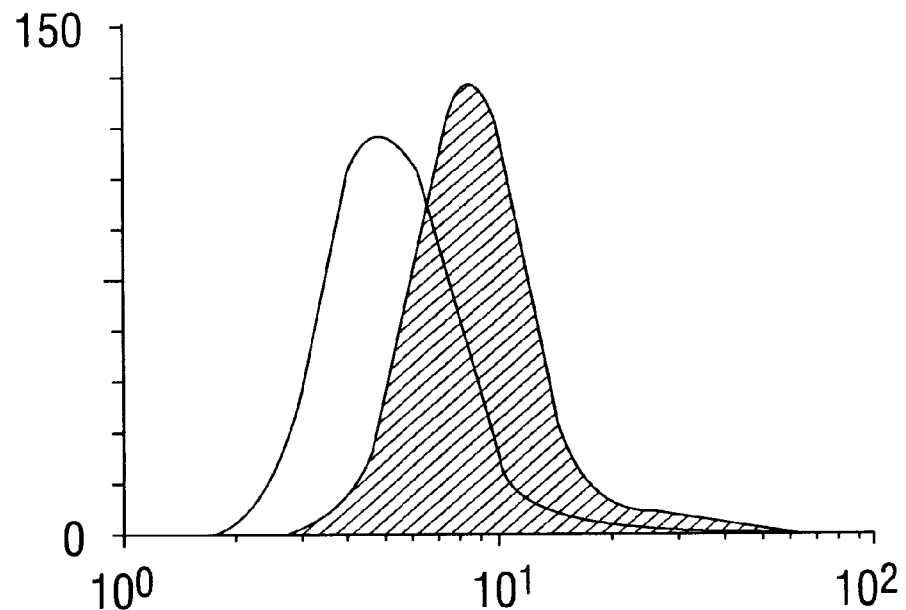
Figure 8C:
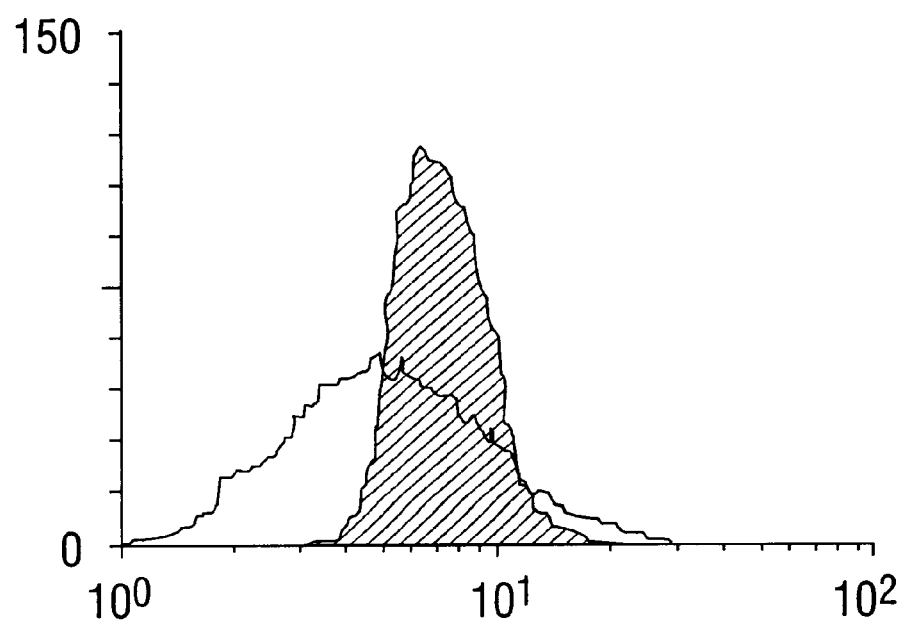

The mechanisms by which ceramide may mediate cell death is yet unknown. Previous studies have demonstrated multiple signaling targets for ceramide, including a serine/threonine kinase (CAPK) and phosphatase (CAPP), PKC isoforms (Lozano et al., 1994), p54 (Kharbanda et al., 1995), and phospholipase D (Gomez-Munoz et al., 1994; Venable et al., 1994). Since changes in oxidative status induced a wide range of cellular responses including growth and apoptosis in WEHI-231 and other lymphocytes, the inhibition of PKC and a resulting accumulation of ceramide were studied for their affect on the level of reactive oxygen species within the cell using the dye dichlorodihydrofluorescein and FACS analysis. As shown in FIG. 8A, surface IgM cross-linking induced a characteristic activation of PKC and generation of reactive oxygen species (ROS) consistent with previously reported data (Blumberg, 1988). Addition of 30 $\mu$M exogenous ceramide (FIG. 8B) or 10 $\mu$M chelerythrine (FIG. 8C) for 15 minutes reduced the ROS in the cells suggesting that the accumulation of ceramide acted as a reducing agent. While non-toxic oxidation may promote cell growth, intracellular reduction may lead to the activation of cysteine proteases which are proposed mediators of apoptosis.

These results demonstrate that inhibition of PKC activity may induce apoptosis in WEHI-231 cells, in part, through activation of a neutral sphingomyelinase and subsequent accumulation of ceramide. It has been previously established that PKC activation by phorbol esters limits ceramide generation and protects cells from apoptosis induced by sphingomyelin hydrolysis (Haimovitz-Friedman et al., 1994a; Gottschalk et al., 1995). These results indicate that PKC activity and ceramide signaling play opposing roles in determining the fate of a cell. The production of ceramide and activation of its apoptotic signaling cascade may represent potentially novel therapeutic targets for enhancing apoptosis in tumor cells.

EXAMPLE 6

Loss of Ceramide Production Confers Resistance to Radiation Induced Apoptosis

The nuclear changes of apoptosis in WEHI-231 JM lymphoma cells following irradiation were examined by staining whole cells with DAPI. Nuclear condensation characteristic of apoptosis following 20 Gy was observed within 24 hours in over 95% of cells quantitated by propidium iodide exclusion and FACScan analysis. In order to assess whether ionizing radiation requires the extranuclear compartment to induce nuclear changes of apoptosis, isolated WEHI-231 JM nuclei were irradiated. Doses from 20 to 40 Gy failed to induce apoptotic changes in either the nuclear membrane or chromatin for over 72 hours following irradiation. Isolated WEHI-231 JM nuclei, however, underwent DNA condensation and nuclear disintegration characteristic of apoptosis within 5 hours following treatment with the kinase inhibitor chelerythrine chloride. These findings demonstrated that nuclear signals alone did not account for apoptosis in intact cells following x-rays and suggested that extranuclear events were required for radiation mediated apoptosis in these cells.

Figure 9A:
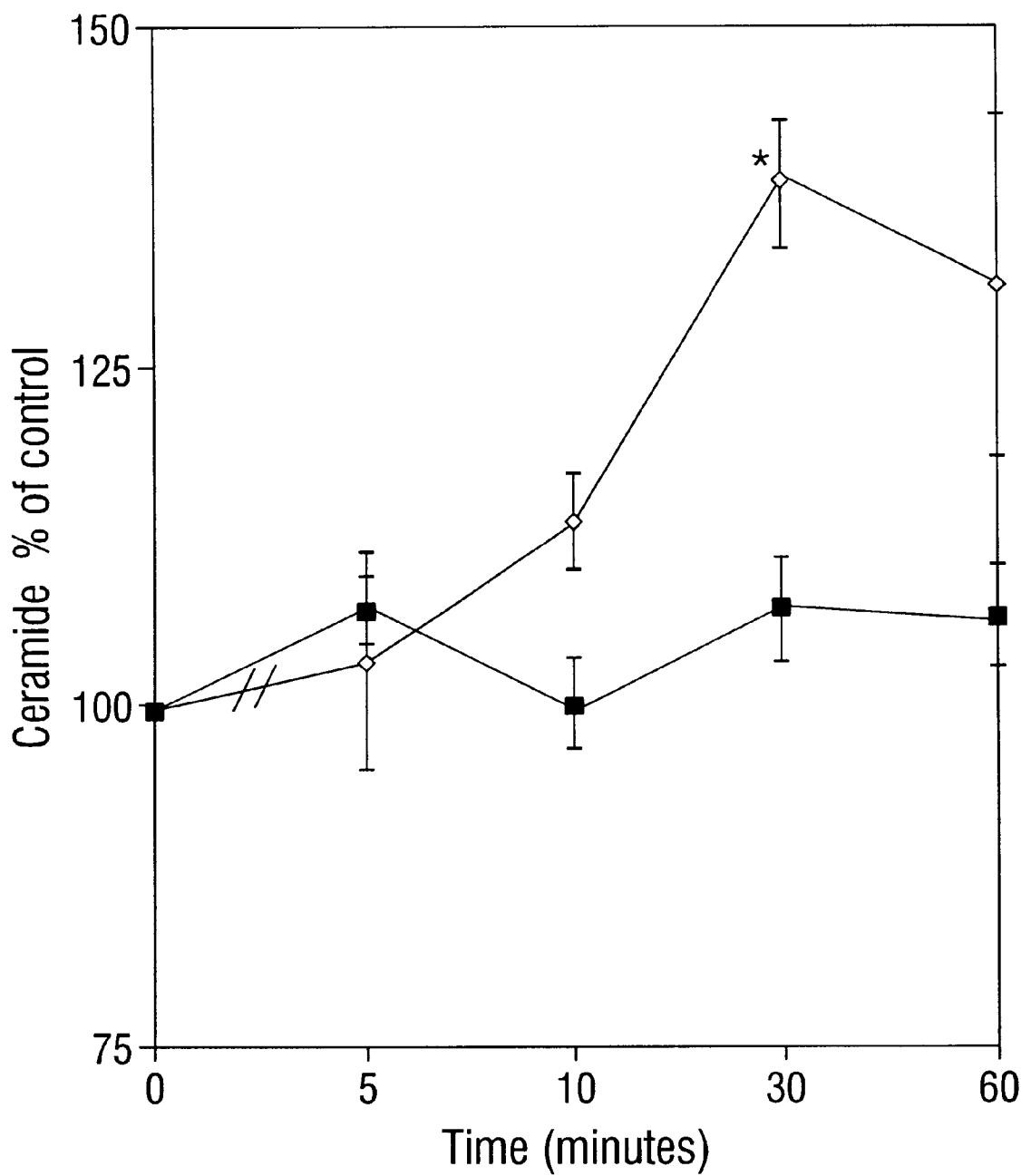
FIG. 9A. Time course for ceramide production in irradiated (8 Gy) WEHI-231 JM (◊) and OE ( ) cells. Data (mean +/– SD) represent at least 4 independent studies in which *p<0.002 compared with unirradiated controls.
Figure 9B:
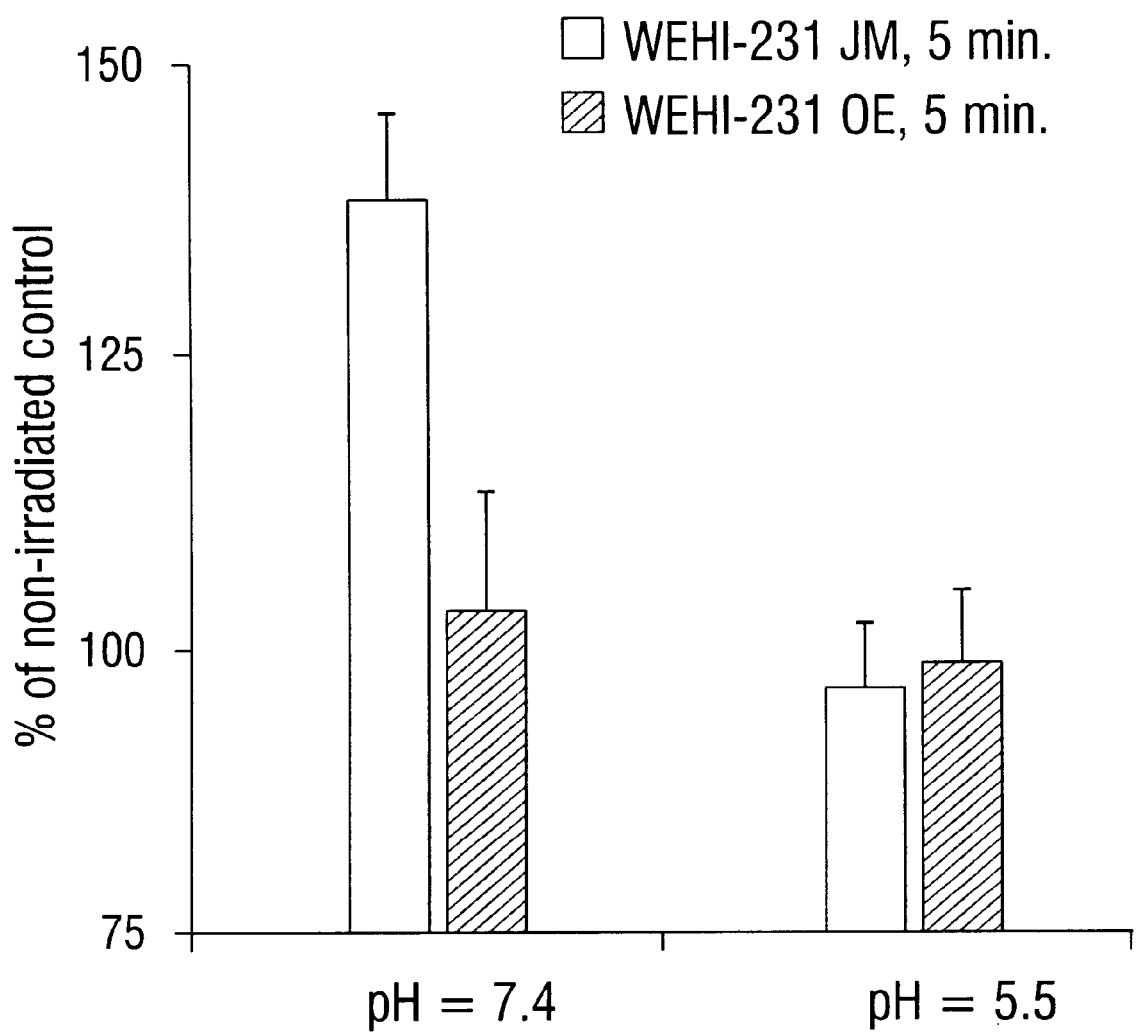
FIG. 9B. Graph of in-vitro neutral and acidic sphingomyelinase activity normalized to percent of control. Data (mean +/– SEM) were derived from 4 independent studies with 2 or more determinants in which p<0.04 for neutral sphingomyelinase activity in WEHI-231 JM cells (Student's t-test) compared with unirradiated controls.

Since ceramide is a proposed extranuclear signal involved in the response to ionizing radiation and other mediators of apoptosis (Dressler et al., 1992; Gottschalk et al., 1995; Ji et al., 1995; Martin et al., 1995), ceramide production following exposure of cells to 8 Gy was measured since this dose of x-rays induces apoptosis in nearly 100% of WEHI-231 within 72 hours. FIG. 9A depicts the time course of ceramide production following irradiation of exponentially growing WEHI-231 JM cells. Ceramide production, measured by the DAG kinase assay, rose to 140% ($p<0.002$) above baseline levels ($78+/-18$ pmols/$10^6$ cells) approximately 30 minutes post x-ray exposure with a concomitant rise in neutral sphingomyelinase activity (FIG. 9B) peaking to 138% ($p<0.04$) of unirradiated control (FIG. 9B). Contrary to other recent reports, acidic sphingomyelinase was unaltered in this cell line from its basal level of 7.6 pmols/mg/min. These findings support a temporal relationship between ceramide production, activation of neutral sphingomyelinase, and the induction of apoptosis following irradiation. While other reports have indicated a dose-response relationship between radiation dose and the production of ceramide, the observed differences in ceramide production between 1 Gy and 8 Gy was not statistically significant.

To determine if the observed increase in ceramide production contributes to radiation mediated apoptosis, a variant WEHI-231 cell line resistant to changes in ceramide production following x-ray exposure was selected. It was deduced that inhibition of ceramidase would select for cells intolerant to the production of ceramide and that n-oleoylethanolamine resistance would result in reduced ceramide production following cellular stresses. WEHI-231 JM cells were incubated with the ceramidase inhibitor n-oleoylethanolamine (Ambrosini et al., 1994). The intracellular accumulation of ceramide compared to baseline levels rose within 24 hours in a dose dependent manner. The resulting cell line, WEHI-231 OE, have similar basal levels of ceramide production ($100+/-10$ pmols/$10^6$ cells) compared to the JM line. FIG. 9B demonstrates the relative increase in ceramide production observed in wild-type WEHI-231 JM cells following exposure to 8 Gy. WEHI-231 OE failed to increase ceramide production compared to unirradiated OE control cells. As observed in the JM line, acidic sphingomyelinase activity (22 pmols/mg/min) was unaltered by ionizing radiation. Thus selection of cells with n-oleoylethanolamine produced a cell line with altered neutral sphingomyelinase activity following ionizing radiation. While the basal levels of ceramide in both cell lines were similar, the OE line failed to increase ceramide production following x-rays.

WEHI-231 OE cells were altered with respect to their apoptotic response following x-irradiation compared with the wild-type WEHI-231 JM cells. The terminal transferase assay (TdT) revealed that at least 50% of WEHI-231 JM cells undergo apoptosis 24 hours following 10 Gy FIG. 10A-1, FIG. 10A-2, FIG. 10A-3, FIG. 10A-4, FIG. 10A-5 and FIG. 10A-6. Too few intact cells remained at 48 hours to carry out further analysis. In contrast, only 12% and 19% of the WEHI-231 OE cells underwent apoptosis at 24 and 48 hours respectively. The WEHI-231 JM parental cell line, but not the WEHI-231 OE line, showed characteristic DNA laddering of apoptosis as early as 14 hours following irradiation which confirmed the TdT results. Taken together, these results demonstrated that development of an apoptosis resistant phenotype could occur through alterations in neutral sphingomyelinase activation and subsequent ceramide generation.

Figure 10B:
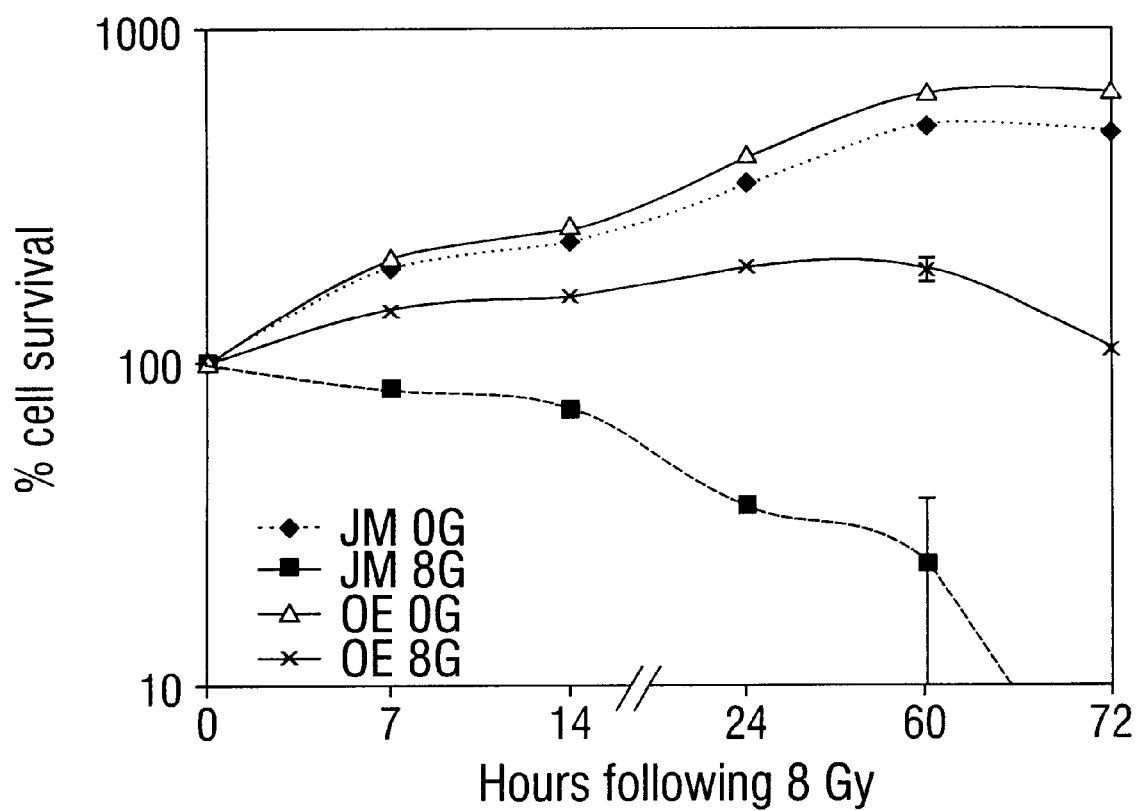
FIG. 10B. WEHI-231 OE cells continue to proliferate following 8 Gy of irradiation. 4–$5 \times 10^5$ exponentially growing JM or OE cells were irradiated and returned to the incubator for time intervals ranging from 6 to 72 hours. At the indicated time points, cells excluding trypan blue were counted using a hemocytometer and scored as viable. Data (mean of at least 2 experiments with duplicate determinants +/– SD) is expressed as a percentage of surviving cells based on the initial count of cells.

Next the decrease in apoptosis was examined to determine whether it would permit the OE line to proliferate following x-irradiation. Following irradiation with 6 Gy, the OE cells continued to proliferate for over 24 hours before entering growth arrest (FIG. 10B). The remaining cells consisted mainly of giant multinucleated cells which lost their ability to exclude vital dyes and eventually fragmented consistent with a post-mitotic death or necrotic cell death (Hall, 1994). The lack of continual OE cell proliferation and subsequent cell death demonstrated that an apoptotic response to ionizing radiation represented only one mechanism by which x-rays kill cells.

Figure 11B:
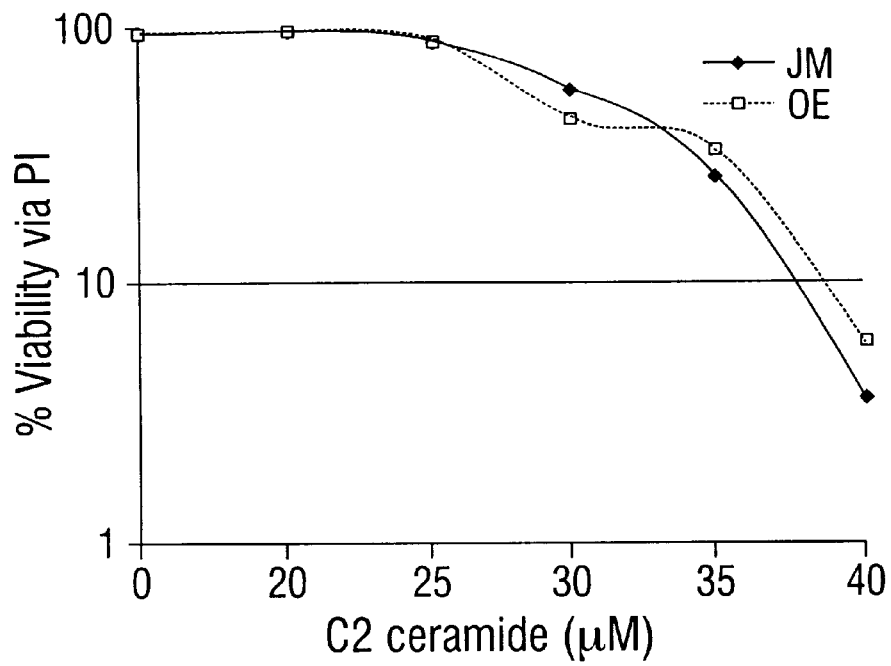
FIG. 11B. WEHI-231 JM and OE cells are equally sensitive to inhibition of sphingosine kinase and exogenous ceramide. Cells were treated with increasing concentrations of C2-ceramide or DL-threo-dihydrosphingosine—a potent inhibitor of sphingosine kinase. Viability was assayed using PI staining and FACS analysis 24 hours after treatment. The graph shows the mean of 3 studies with duplicate determinants.
Figure 11C:
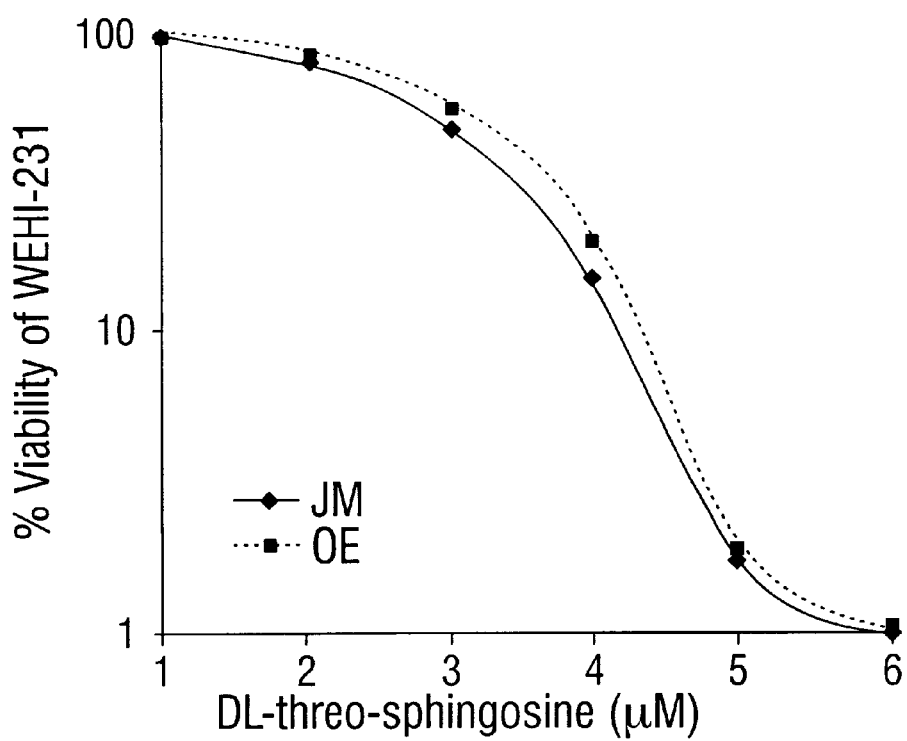

In order to address the question of whether the resistance of the OE subline was due, in part, to alterations in ceramide metabolites or targets, three studies were performed. Pretreatment of irradiated WEHI-231 OE cells with the cell permeable ceramide analog C2-ceramide restored the apoptotic response at 24 hours FIG. 11A-1, FIG. 11A-2, and FIG. 11A-3. In addition, WEHI-231 JM and OE cells were equally sensitive (FIG. 11B) to exogenous ceramide ($IC_{50}=3$ $\mu M$) and to the sphingosine kinase inhibitor DL-threo-dihydrosphingosine ($IC_{50}=3$ $\mu M$) which is reported to specifically inhibit sphingosine-1-phosphate formation—a ceramide metabolite reported to suppress the apoptotic effects of ceramide production (Cuvillier et al., 1996). Both cell lines were equally susceptible to the effects of sphingosine kinase inhibition and the resulting decrease in ceramide. These results demonstrated that cellular components which interact with ceramide and induce apoptosis remained unaltered in WEHI-231 OE cells. Thus the radioresistance can be attributed to the lack of sphingomyelinase activation and the subsequent decreased ceramide production following irradiation.

These results demonstrate that the extranuclear compartment contributed an essential apoptotic signal following exposure of cells to ionizing radiation. Consistent with these data are studies demonstrating that extranuclear signals are required to induce the characteristic cytoplasmic and nuclear changes of apoptosis in mammalian cells (Raff et al., 1994; Jacobson et al., 1994). These data suggest that acquired defects in ceramide production from sphingomyelin hydrolysis can result in a radioresistant phenotype. Specifically, the loss of neutral, but not acidic sphingomyelinase activity, is associated with resistance to apoptosis following ionizing radiation in contrast to previous studies in acidic sphingomyelinase knockout mice (Santana et al., 1996) which implicated the acidic sphingomyelinase as the main effector of apoptosis.

The acidic sphingomyelinase activity in the exponentially growing JM and OE lines was low compared to other published cell lines and failed to increase following ionizing radiation. The lack of activation following x-rays and the relatively low basal levels of activity suggest that it is not a component of the apoptotic response to x-rays in this system. These data taken together further the evidence that the loss of ceramide production from neutral sphingomyelinase may represent a mechanism by which some cell types develop resistance to x-rays.

The conversion of sphingosine to sphingosine-1-phosphate has been shown to inhibit ceramide induced apoptosis (Cuvillier et al., 1996). Thus, other lipid metabolites of ceramide may oppose the death pathway, as recently suggested by Cuvillier et al. (1996). These studies demonstrate that increased sphingosine kinase activity may represent an alternative way cells may acquire resistance to x-rays. These data demonstrated that both the radioresistant and wild-type cell lines are equally sensitive to both exogenous ceramide and inhibition of sphingosine kinase and further support the hypothesis that the loss of the ceramide signaling event following x-rays is responsible for the resistant phenotype, suggesting that tumor cells may become resistant to apoptosis in-vivo through a similar mechanism.

While a loss of neutral sphingomyelinase activation and ceramide generation prevents apoptosis, the OE cell line undergoes a mitotic or divisional death at a later time. The early apoptotic response of JM cells to undergo apoptosis following ionizing radiation is dependent, in part, on activation of neutral sphingomyelinase and an increase in ceramide production. The lack of continued cell proliferation beyond the first or second mitotic division, however, is consistent with previous studies which demonstrate that x-irradiation kills tumor cells through several mechanisms (Dewey et al., 1995; Szumiel, 1994; Kolesnick et al., 1994) (Aldridge et al., 1995).

Ceramide production is proposed to mediate cell killing by several other DNA damaging agents including daunorubicin and 1-β-D-arabinofuranosylcytosine (ara-C) (Strum et al., 1994; Bose et al., 1995). Loss of ceramide production may therefore represent a generalized mechanism of resistance to several forms of antineoplastic therapies considered to damage DNA. Conventional strategies have thus far focused on the use of DNA damaging agents to act as radiosensitizers (Vokes and Weichselbaum, 1990; Horton et al., 1995). These data also suggest that increasing ceramide production to induce apoptosis may be an additional strategy for cell killing in cancer therapy.

EXAMPLE 7

Radio-resistant Cells, Immune to Other Inducers of Apoptosis, are not Immune to Chelerythrine Induced Apoptosis Using the procedures already described (Chmura, 1996; Chmura et al., 1996a; Chmura et al., 1996b), three different apoptosis-resistant cell lines were examined for their susceptibility to apoptosis induced by chelerythrine. The three cell lines used were bcl-x WEHI-231, which represents WEHI-231 cells that have been transfected with bcl-x and are highly resistant to radiation induce apoptosis, MG cells and the WEHI-231 OE (JM) cells previously described.

All three cell lines were treated with chelerythrine and x-irradiation as previously described (Chmura et al., 1996a; Chmura et al., 1996b) with the following modifications. Cells were pre-exposed to YVAD-cmk (100 μM), a protease inhibitor of the interleukin 1-b converting enzyme (ICE) subfamily or to ZVAD (20 μM), which inhibits the cpp32β family of proteases, for 30 minutes before being subjected to chelerythrine.

Figure 12:
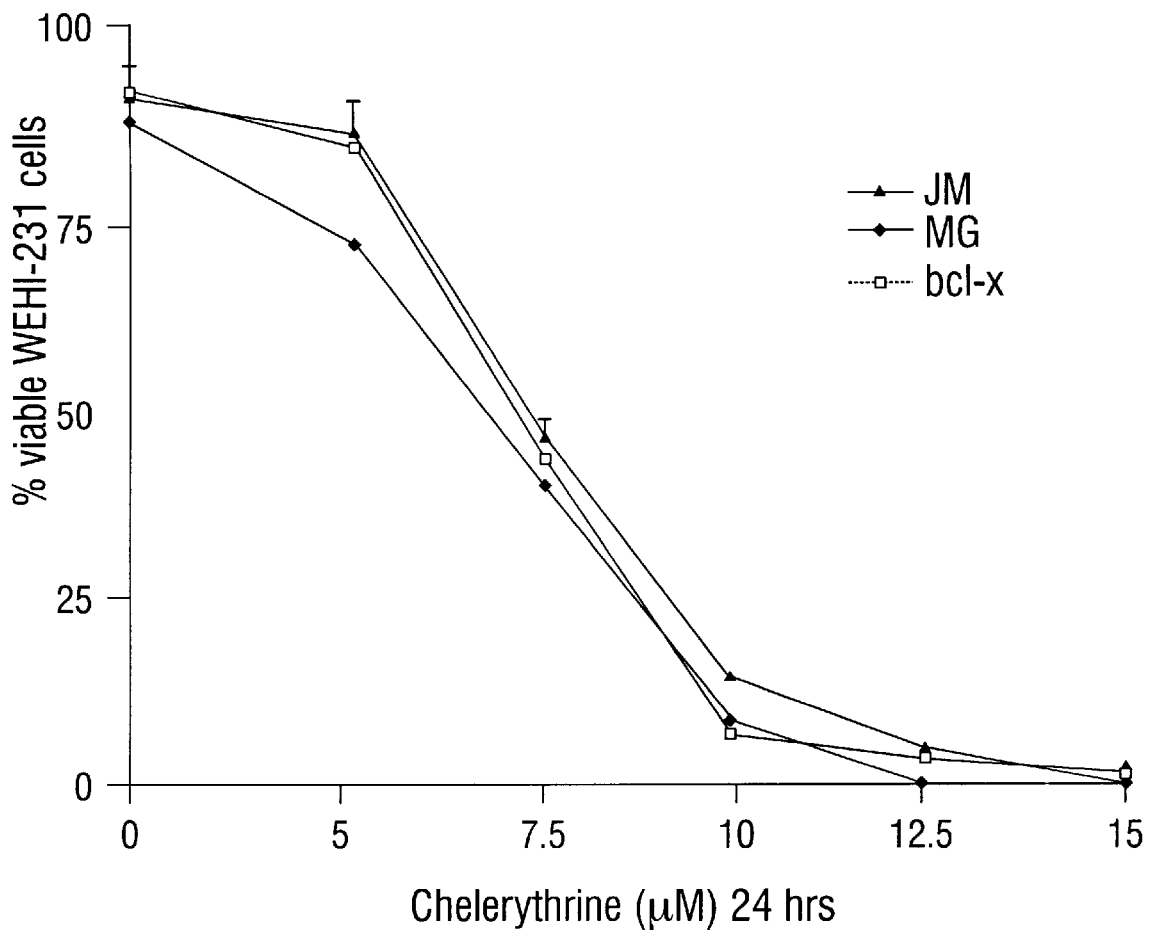
FIG. 12. Viability of resistant WEHI-231 OE (JM) MG (MG) and WEHI-231 cells transfected with bcl-x (bcl-x) cells exposed to increasing concentrations of chelerythrine 30 minutes after exposure.

Surprisingly, overexpression of the anti-apoptotic protein bcl-x did not block chelerythrine induced apoptosis (FIG. 12). This result is unexpected because bcl-x is able to block the induction of apoptosis by most known apoptotic inducers (Boise et al., 1995; Chen et al., 1995; Choi et al., 1995; Dtta et al., 1996; Datta et al. 1995; Emoto et al., 1995). The other two cell lines also were not resistant to chelerythrine (FIG. 12).

Exposure to YVAD-cmk did not prevent chelerythrine induced apoptosis, even at low doses of chelerythrine. But exposure to ZVAD did block chelerythrine induced apoptosis, even at doses>15 μM chelerythrine. These results suggest that bcl-x protects from upstream of cpp32β to prevent apoptosis and that chelerythrine directly activates the protease cpp32β.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

Aldridge, Arends, Radford, "Increasing the susceptibility of the rat 208 F fibroblast cell line to radiation-induced apoptosis does not alter its clonogenic survival dose-response," *Br. J. Cancer,* 71:571–577, 1995.

Ambrosini, Bertoli, Tanfani, Wozniak, Zolese, "The effect of N-acyl ethanolamines on phosphatidylethanolamine phase transitions studied by laurdan generalised polarisation," *Chem. Phys. Lipids,* 72:127–34, 1994.

Bertrand et al., "Induction of a common apoptotic pathway," *Exp. Cell Res.,* 211:314–321, 1993.

Bertrand, Solary, Kohn, Pommier, "Staurosporine may activate a common final patheway to apoptosis," *Proc. Am. Assoc. Cancer Res.,* 34:1735, 1994.

Blumberg, "Protein Kinase C as the receptor for the phorbol ester tumor promoters," *Cancer Res.,* 48:1–8, 1988.

Boise, Gottschalk, Quintans, Thompson, "Bcl-2 and Bcl-2-related proteins in apoptosis regulation," *Curr. Top MicrobioL Immunol.,* 200:107–21, 1995.

Boothman, Bouvard, Hughes, *Cancer Res.,* 49:2871–2878, 1989.

Borchardt, Lee, Kalen, Bell, "Growth-dependent regulation of cellular ceramides in human T-cells," *Biochem. Biophys Acta.,* 1212:327–36, 1994.

Borek, *Pharmacol. Ther.,* 27:99–142, 1985.

Bose, Verheij, Haimovitz-Friedman, Scotto, Fuks, Kolesnick, "Ceramide synthase mediates daunorubicin-induced apoptosis: an alternative mechanism for generating death signals," *Cell,* 82:405–14, 1995.

Brachman et al., "p53 mutation does not correlate with radiosensitivity in 24 head and neck cancer cell lines," *Cancer Res.,* 53:3667–9, 1993.

Bussink, Tofilon, Brock, "Repair of chromosome and DNA breaks versus cell survival in Chinese hamster cells," *Int. J. Radiat. Biol.,* 70:23–3, 1996.

Chang and Little, "Delayed reproductive death in X-irradiated Chinese hamster ovary cells," *Int. J. Radiat. Biol.,* 60:483–96, 1991.

Chang and Little, "Delayed reproductive death as a dominant phenotype in cell clones surviving X-irradiation," *Carcinogenesis,* 13:923–8, 1992a.

Chang and Little, "Evidence that DNA double-strand breaks initiate the phenotype of delayed reproductive death in Chinese hamster ovary cells," *Radiat. Res.,* 131:53–9, 1992b.

Chen, Quintans, Fuks, Thompson, Kufe, Weichselbaum, "Suppression of Bcl-2 messenger RNA production may mediate apoptosis after ionizing radiation, tumor necrosis factor alpha, and ceramide," *Cancer Res.,* 55:991–4, 1995.

Chmura, "Comparison of Terminal transferase, 7-actinomycin D, and Propidium Iodide for the detection of apoptosis in Lymphocytes," *In: Immunology Methods Manual,* I. Lefkovits (ed.), Academic Press, 1996.

Chmura Nodzenski, Crane, Hallahan, Weichselbaum, Quintans, "Cross-talk between ceramide and PKC activity in the control of apoptosis," *Adv. Experi. Medical Biol.* 406:39–55, 1996a.

Chmura, Nodzenski, Quintans, Weischelbaum, "PKC inhibition induces apoptosis and ceramide production through a neutral sphingomyelinase," *Cancer Research,* 56:2711–2714, 1996b.

Choi, Boise, Gottschalk, Quintans, Thompson, Klaus, "The role of bcl-XL in CD40-mediated rescue from anti-mu-induced apoptosis in WEHI-231 B lymphoma cells," *Eur. J. Immunol,* 25:1352–7, 1995.

Coroneos et al., "Differential regulation of sphingomyelinase and ceramidase activities by growth factors and cytokines. Implications for cellular proliferation and differentiation." *J. Biol. Chem.* 270:23305–23309, 1995.

Cotter, Lennon, Clynn, Green, "Microfilament-disrupting agents prevent the formation of apoptotic bodies in tumor cells undergoing apoptosis," *Cancer Res.,* 52:997–1005, 1992.

Cuvillier, Pirianov, Kleuser, Vanek, Coso, Spiegel, "Suppression of ceramide mediated programmed cell death by sphingosine-1-phosphate," *Nature,* 381:800–803, 1996.

Datta, Manome, Taneja, Boise, Weichselbau, Thompson, Slapak, Kufe, "Overexpression of Bcl-XL by cytotoxic drug exposure confers resistance to ionizing radiation-induced internucleosomal DNA fragmentation," *Cell Growth Differ.,* 6:363–370, 1995.

Datta, Banach, Kojima, Talanian, Alnenri, Wong, Kufe, "Activation of the CPP32 protease in apoptosis induced by 1-beta-D-arabinofuranosylcytosine and other DNA-damaging agents," *Blood,* 88:1936–43, 1996.

Datta, R. et al., *J. Biol. Chem.* 272:1965–1969, 1997.

Dewey, Ling, Meyn, "Radiation-induced apoptosis: relevance to radiotherapy," *Int. J. Radiat. Oncol. Biol. Phys.,* 33:781–96, 1995.

Dressler and Kolesnick "Ceramide-1-Phosphate, A Novel Phospholipid in Human Leukemia (HL-60) Cells," *J. Biol. Chem.,* 265:14921–14917, 1990.

Dressler, Mathias, Kolesnick, "Tumor necrosis factor-alpha activates the sphingomyelin signal transduction pathway in a cell-free system," *Science,* 255:1715–18, 1992.

Emoto, Manome, Meinhardt, Kisaki, Kharbanda, Robertson, Ghayur, Wong, Kamen, Weichselbaum, et al., "Proteolytic activation of protein kinase C delta by an ICE-like protease in apoptotic cells," *EMBO J.,* 14:6148–56, 1995.

Forbes et al., "Induction of apoptosis in chronic lymphocytic leukemia cells and its prevention by phorbol diester," *Exp. Cell Res.,* 198:367–371, 1992.

Fuks, Persaud, Alfieri, McLoughlin, Ehleiter, Schwartz, Seddon, Cordon-Cardo, Haimovitz-Friedman, "Basic Fibroblast Growth Factor Protects Endothelial Cells Against Radiation-induced Programmed Cell Death In Vitro and In Vivo," *Cancer Res.,* 54:2582–2590, 1994.

Gomez-Munoz, Martin, O'Brien, Brindley, "Cell-permeable ceramides inhibit the stimulation of DNA synthesis and phospholipase D activity by phosphatidate and lysophosphatidate in rat fibroblasts," *J. Biol. Chem.,* 269:18384–9, 1994.

Gorczyca et al., *Cancer Res.,* 53:1945–1951, 1993.

Gottschalk and Quintans "Apoptosis in B Lymphocytes: The WEHI-231 perspective," *Immunol. Cell Biol.,* 73:41–49, 1995.

Gottschalk, McShan, Merino, Quintans, "Physiological cell death in B Lymphocytes: Differential susceptibility of WEHI-231 sublines to anti-Ig induced PCD and lack of correlation with bcl-2 expression," *Inter. Immun.,* 6:121–30, 1993.

Gottschalk, Boise, Thompson, Quintans, "Identification of irnmunosuppressant-induced apoptosis in a murine B-cell line and its prevention by bcl-x but not bcl-2," *Proc. Natl. Acad. Sci. USA,* 91:7350–4, 1994.

Gottschalk McShan, Kilkus, Dawson, Quintans, "Resistance to anti-IgM-induced apoptosis in a WEHI-231 subline is due to insufficient production of ceramide," *Eur. J. of Immun.,* 25:1032–8, 1995.

Gray et al., "Alkaloid, Lignan and Sterol Constituents of Zanthoxylum simulans", *Planta Medica* 39:209, 1980.

Haggerty and Monroe, "A mutant of the WEHI-231 B lymphocyte line that is resistant to phorbol esters is still sensitive to antigen receptor-mediated growth inhibition," *Cell. Immun.,* 154:166–80, 1994.

Haimovitz-Friedman Kan, Fuks Kolesnick, "Ionizing radiation acts on cellular membranes to generate ceramide and initiate apoptosis," *J. Exp Med.,* 180:525–35, 1994a.

Haimovitz-Friedman, Balaban, McLoughlin, Ehleiter, Michaeli, Vlodavsky, Fuks, "Protein kinase C mediates basic fibroblast growth factor protection of endothelial cells against radiation-induced apoptosis," *Cancer Res.,* 54:2591–7, 1994b.

Hall, *Radiobiology for the Radiologist,* Harper and Row, 1988.

Hall, *Radiobiology for the Radiologist,* Harper and Row, 1994.

Hallahan, Beckett, Kufe, et al., *Int. J. Rad. Onc. Biol.,* 19:69–74, 1990.

Hallahan, Virudachalam, Schwartz, Panje, Mustafi, Weischselbaum, "Inhibition of protein kinases sensitizes human tumor cells to ionizing radiation,"*Radiat. Res.,* 129:345–50, 1992.

Hallahan, Virudachalam, Kuchibhotla, Kufe, Weichselbaum, "Membrane-derived second messenger regulates x-ray-mediated tumor necrosis factor alpha gene induction," *Proc. Natl. Acad. Sci. USA.,* 91:4897–901, 1994.

Hallahan et. al., "C-jun and Egr-1 participate in DNA synthesis and cell survival in response to ionizing radiation exposure," *J. Biol. Chem.*, 270:30303–30309, 1995.

Harmon and Allan, "X-ray-induced cell death by apoptosis in the immature rat cerebellum," *Scanning Microsc.*, 2:561–8, 1988.

Herbert, Augereau, Gleye, Maffrand, "Chelerythrine is a potent and specific inhibitor of protein kinase C," *Biochem. Biophys. Res. Commun.*, 172:993–9, 1990.

Horton, Srivastava, Smudzka, Wilson, "Strategic down-regulation of DNA polymerase beta by antisense RNA sensitizers mammalian cells to specific DNA damaging agents," *Nucleic Acids Res.*, 23:3810–5, 1995.

Indap and Rao, "Cell death by apoptosis and cancer chemotherapy," *Natl. Med. J. India*, 8:65–7, 1995.

Jacobson, Burne, Raff, "Programmed cell death and Bcl-2 protection in the absence of a nucleus," *Embo. J.*, 13:1899–910, 1994.

Jarvis and Kolesnick, "Ceramide and the induction of apoptosis," *Clinical Cancer Research*, 2:1–6, 1996.

Jarvis, Kolesnick, Fornari, Traylor, Gewirtz, Grant, "Induction of apoptotic cell death by sphingomyelinase and ceramide in a variety of mammalian cells," *Proc. Natl. Acad. Sci. USA*, 91:73–77, 1994.

Ji, Zhang, Hirabayashi, "Inhibition of tumor necrosis factor alpha- and ceramide-induced intemucleosomal DNA fragmentation by herbimycin A in U937 cells," *Biochem. Biophys. Res. Commun.*, 212:640–7, 1995.

Jones and Murray, "Evidence that ceramide selectively inhibits protein kinase C-alpha translocation and modulates bradykinin activation of phospholipase D," *J. Biol. Chem.*, 270:5007–13, 1995.

Kharbanda, Ren, Pandey, Shafman, Kyriakis, Weichselbaum, Kufe, "Activation of the c-Abl tyrosine kinase in the stress response to DNA-damaging agents," *Nature*, 376:375–8, 1995.

Kobayashi, Nakano, Morimito, Tamaoki, "Calphostin C a novel microbial compound and highly potent protein kinase C inhibitor," *Biochem. Biophys. Res. Commun.*, 159:548–53, 1989.

Kolesnick, "Sphingomyelinase action inhibits phorbol ester-induced differentiation of human promyelocytic leukemic (HL-60) cells," *J. Biol. Chem.*, 264:7617–23, 1989.

Kolesnick, "Signal transduction through the sphingomyelin pathway," *Mol. Chem. Neuropathol.*, 21:287–97, 1994.

Kolesnick, Haimovitz-Friedman, Fuks, "The sphingomyelin signal transduction pathway mediates apoptosis for tumor necrosis factor, Fas, and ionizing radiation," *Biochem. Cell. Biol.*, 72:471–4, 1994.

Kondratyev, Chung, Jung, "Identification and characterization of a radiation-inducible glycosylated human early-response gene," *Cancer Res.*, 56:1498–1502, 1996.

Lambert and Borek, *J. Natl. Cancer Inst.*, 80:1492–1497, 1988.

Long, et al., *J. Clin. Invest.*, 82:1779, 1988.

Lowe, Ruley, Jacks, Housman, "p53-dependent apoptosis modulates the cytotoxicity of anticancer agents," *Cell*, 74:957–67, 1993a.

Lowe, Schmitt, Smith, Osborne, Jacks, "p53 is required for radiation-induced apoptosis in mouse thymocytes," *Nature*, 362:847–9, 1993b.

Lowe et al., "p53 status and the efficacy of cancer therapy in vivo," *Science*, 266:807–10, 1994.

Lozano, Berra, Municio, Diaz-Meco, Dominguez, Sanz, Moscat, "Protein kinase C zeta isoform is critical for kappa B-dependent promoter activation by sphingomyelinase," *J. Biol. Chem.*, 269:19200–07, 1994.

Magnuson et. al., "Protein Kinase C—an enzyme and its relatives," *Semin. Cancer Biol.*, 5:277–284, 1994.

Maity, McKenna, Muschel, "The molecular basis for cell cycle delays following ionizing radiation: a review," *Radiother. Oncol.*, 31:1–13, 1994.

Martin and Green, "Apoptosis as a goal of cancer therapy," *Curr. Opin. Oncol.*, 6:616–21, 1994.

Martin, Newmeyer, Mathias, Farschon, Wang, Reed, Kolesnick, Green, "Cell-free reconstitution of Fas-, UV radiation- and ceramide-induced apoptosis," *Embo J.*, 14:5191–200, 1995.

McKenna, Iliakis, Weiss, Bernhard, Muschel, "Increased G2 delay in radiation-resistant cells obtained by transformation of primary rat embryo cells with the oncogenes H-ras and v-myc," *Radiat. Res.*, 125:283–7, 1991.

Meyn et. al., "Biochemical modulation of radiation-induced apoptosis in murine lymphoma cells," *Radiat. Res.*, 136:327–34, 1993.

Meyn, Stephens, Hunter, Ang, Milas, "Reemergence of apoptotic cells between fractionated doses in irradiated murine tumors," *Int. J. Radiat. Oncol. Biol. Phys.*, 30:619–624, 1994.

Meyn, Stephens, Hunter, Milas, "Apoptosis in murine tumors treated with chemotherapy agents," *Anticancer Drugs*, 6:443–50, 1995.

Nagasawa, Keng, Harley, Dahlberg, Little, "Relationship between gamma-ray-induced G2/M delay and cellular radiosensitivity," *Int. J. Radiat. Biol.*, 66:373–379, 1994.

Nagata and Golstein, "The Fas death factor," *Science*, 267:1449–52, 1995.

Obeid, Linardic, Karolak, Hannun, "Programmed Cell Death Induced by Ceramide," *Science*, 259:1769–71, 1993.

Ohta, Yatomi, Sweeney, Igarashi, "A possible role of sphingosine in induction of apoptosis by tumor necrosis factor-alpha in human neutrophils," *FEBS Lett.*, 355:267–270, 1994.

Ojeda, Guarda, Maldonato, Folch, "Protein kinase C involvement in thymocyte apoptosis induced by hydrocortisone," *Cell. Immunol.*, 125:535–539, 1990.

Park, "Expression of human RAD52 confers resistance to ionizing radiation in mammalian cells," *J. Biol. Chem.*, 270:15467–15470, 1995.

Preiss, Loomis, Bishop, Stein, Niedel, Bell, "Quantitative Measurement of Sn-1,2-Diacylglycerols Present in Platelets," *J. Biol. Chem.*, 261:8597–600, 1986.

Quintans, Kilkus, McShan, Gottschalk, Dawson, "Ceramide mediates the apoptotic response of WEHI 231 cells to anti-immunoglobulin, corticosteroids and irradiation," *Biochem. Biophys. Res. Commun.*, 202:710–4, 1994.

Radford and Murphy, "Radiation response of mouse lymphoid and myeloid cell lines. Part III. Different signals can lead to apoptosis and may influence sensitivity to killing by DNA double-strand breakage," *Int. J. Radiat. Biol.*, 65:229–39, 1994.

Raff et al., "Programmed cell death and the control of cell survival," *Philos. Trans. R. Soc. Lond. B. Biol. Sci.,* 345:265–8, 1994.

Rosenthal et. al., "Phase I studies of continuous-infusion paclitaxel given with standard aggressive radiation therapy for locally advanced solid tumors," *Semin. Oncol.,* 22:13–17, 1995.

Rotenberg, Zhu, Su, Riedel, "Deletion analysis of protein kinase C inactivation by calphostin C," *Mol. Carcin.,* 12:42–9, 1995.

Sanchez and Elledge, "Stopped for repairs," *Bioessays,* 17:545–8, 1995.

Santana et. al., "Acid Sphingomyelinase Deficient Human Lymphoblasts and Mice are defective in Radiation-Induced Apoptosis," *Cell,* 88:189–199, 1996.

Shen, Cloud, Chen, Park, "Specific interactions between the human RAD51 and RAD52 proteins," *J. Biol. Chem.,* 271:148–152, 1996.

Stephens, Ang, Schultheiss, Milas, Meyn, "Apoptosis in Irradiated Murine Tumors," *Radiation Research,* 127:308–136, 1991.

Stephens, Hunter, Ang, Milas, Meyn, "Development of apoptosis in irradiated murine tumors as a function of time and dose," *Radiat. Res.,* 135, 75–80, 1993.

Strum, Small, Pauig, Daniel, "1-beta-D-Arabinofuranosylcytosine stimulates ceramide and diglyceride formation in HL-60 cells," *J. Biol. Chem.,* 269:15493–7, 1994.

Szumiel, "Ionizing radiation-induced cell death," *Int. J. Radiat. Biol.,* 66:329–41, 1994.

Thompson and Fields, "betaII protein kinase C is required for the G2/M phase transition of cell cycle," *J. Biol. Chem.,* 271:15045–15053, 1996.

Uckun, Evans, Forsyth, Waddick, Ahlgren, Chelstrom, Burkhardt, Bolen, Myers, "Biotherapy of B-cell precursor leukemia by targeting genistein to CD19-associated tyrosine kinases," *Science,* 267:886–91, 1995.

Venable, Blobe, Obeid, "Identification of a defect in the phospholipase D/diacylglycerol pathway in cellular senescence," *J. Biol. Chem.,* 269:26040–9, 1994.

Verheij, Haimovitz-Friedman, Fuks, Kolesnick, "Requirement for ceramide initiated SAPK/JNK signaling in stress-induced apoptosis," *Nature,* 380:75–78, 1996.

Vokes and Weichselbaum, "Concomitant chemoradiotherapy: rationale and clinical experience in patients with solid tumors," [published erratum appears in J Clin Oncol Aug. 8, 1990;(8):1447]," *J. Clin. Oncol.,* 8:911–34,1990.

Wiegmann, Schutze, Machleidt, Witte, Kronke, "Functional dichotomy of neutral and acidic sphingomyelinases in tumor necrosis factor signaling," *Cell,* 78:1005–15, 1994.

Witte, Fuks, Haimovitz-Friedman, Vlodavsky, Goodman, Eldor, *Cancer Res.,* 49:5066–5072, 1989.

Young, Murtha, Zhang, "Tumor-promoting phorbol ester-induced cell death and gene expression in a human prostate adenocarcinoma cell line," *Oncol. Res.,* 6:203–10, 1994.

What is claimed is:

1. A method for inhibiting growth of a tumor cell comprising contacting said tumor cell with chelerythrine and contacting said tumor cell with ionizing radiation, wherein the dose of said chelerythrine, when combined with the dose of ionizing radiation, is effective to inhibit growth of said tumor cell.

2. The method of claim 1, wherein said chelerythrine is contacted with said tumor cell prior to contacting said tumor cell with said ionizing radiation.

3. The method of claim 1, wherein said ionizing radiation is contacted with said tumor cell prior to contacting said tumor cell with said chelerythrine.

4. The method of claim 1, wherein said chelerythrine and said ionizing radiation are contacted with said tumor cell simultaneously.

5. The method of claim 1, wherein said dose of chelerythrine is about 0.5 mg/kg to about 10 mg/kg.

6. The method of claim 5, wherein said dose of chelerythrine is about 1 mg/kg to about 4 mg/kg.

7. The method of claim 1, wherein said ionizing radiation is selected from the group consisting of $\gamma$-irradiation, x-irradiation, microwave irradiation and ultraviolet irradiation.

8. The method of claim 1, wherein said total dose of ionizing radiation is about 1 Gy to about 80 Gy.

9. The method of claim 8, wherein said total dose of ionizing radiation is about 70 Gy.

10. The method of claim 1, wherein said chelerythrine is contacted with said tumor cell at least twice.

11. The method of claim 1, wherein said ionizing radiation is contacted with said tumor cell at least twice.

12. The method of claim 1, wherein said tumor cell is selected from the group consisting of a skin cancer cell, a prostate cancer cell, a lung cancer cell, a brain cancer cell, a breast cancer cell, an ovarian cancer cell, a cervical cancer cell, a liver cancer cell, a pancreatic cancer cell, a colon cancer cell, a stomach cancer cell and a leukemia cell.

13. The method of claim 1, wherein said tumor cell is a human tumor cell.

14. The method of claim 13, wherein said human tumor cell is located in a human patient.

15. The method of claim 14, wherein said chelerythrine is administered systemically.

16. The method of claim 14, wherein said chelerythrine is administered locally to a tumor mass containing said tumor cell.

17. The method of claim 14, wherein said chelerythrine is administered directly to a tumor mass containing said tumor cell.

18. The method of claim 14, wherein said chelerythrine is administered to a resected tumor bed containing said tumor cell.

19. The method of claim 14, wherein said ionizing radiation is administered to the entire patient.

20. The method of claim 14, wherein said ionizing radiation is administered locally to a tumor mass containing said tumor cell.

21. A method of inducing apoptosis in a tumor cell comprising contacting said tumor cell with chelerythrine and contacting said tumor cell with ionizing radiation, wherein the dose of said chelerythrine, when combined with the dose of ionizing radiation, is effective to induce apoptosis in said tumor cell.

22. The method of claim 21, wherein said chelerythrine is contacted with said tumor cell prior to contacting said tumor cell with said ionizing radiation.

23. The method of claim 21, wherein said ionizing radiation is contacted with said tumor cell prior to contacting said tumor cell with said chelerythrine.

24. The method of claim 21, wherein said chelerythrine and said ionizing radiation are contacted with said tumor cell simultaneously.

25. The method of claim 21, wherein said dose of chelerythrine is about 0.5 mg/kg to about 10 mg/kg.

26. The method of claim 25, wherein said dose of chelerythrine is about 1 mg/kg to about 4 mg/kg.

27. The method of claim 21, wherein said ionizing radiation is selected from the group consisting of γ-irradiation, x-irradiation, microwave irradiation and ultraviolet irradiation.

28. The method of claim 21, wherein said total dose of ionizing radiation is about 1 Gy to about 80 Gy.

29. The method of claim 28, wherein said total dose of ionizing radiation is about 70 Gy.

30. The method of claim 21, wherein said chelerythrine is contacted with said tumor cell at least twice.

31. The method of claim 21, wherein said ionizing radiation is contacted with said tumor cell at least twice.

32. The method of claim 21, wherein said tumor cell is selected from the group consisting of a skin cancer cell, a prostate cancer cell, a lung cancer cell, a brain cancer cell, a breast cancer cell, an ovarian cancer cell, a cervical cancer cell, a liver cancer cell, a pancreatic cancer cell, a colon cancer cell, a stomach cancer cell and a leukemia cell.

33. The method of claim 21, wherein said tumor cell is a human tumor cell.

34. The method of claim 33, wherein said human tumor cell is located in a human patient.

35. The method of claim 34, wherein said chelerythrine is administered systemically.

36. The method of claim 34, wherein said chelerythrine is administered locally to a tumor mass containing said tumor cell.

37. The method of claim 34, wherein said chelerythrine is administered directly to a tumor mass containing said tumor cell.

38. The method of claim 34, wherein said chelerythrine is administered to a resected tumor bed containing said tumor cell.

39. The method of claim 34, wherein said ionizing radiation is administered to the entire patient.

40. The method of claim 34, wherein said ionizing radiation is administered locally to a tumor mass containing said tumor cell.

41. A method of killing a tumor cell comprising contacting said tumor cell with chelerythrine and contacting said tumor cell with ionizing radiation, wherein the dose of said chelerythrine, when combined with the dose of ionizing radiation, is effective to kill said tumor cell.

42. The method of claim 41, wherein said dose of chelerythrine is about 0.5 mg/kg to about 10 mg/kg.

43. The method of claim 42, wherein said dose of chelerythrine is about 1 mg/kg to about 4 mg/kg.

44. The method of claim 41, wherein said ionizing radiation is selected from the group consisting of γ-irradiation, x-irradiation, microwave irradiation and ultraviolet irradiation.

45. The method of claim 41, wherein said total dose of ionizing radiation is about 1 Gy to about 80 Gy.

46. The method of claim 45, wherein said dose of ionizing radiation is about 70 Gy.

47. The method of claim 41, wherein said chelerythrine is contacted with said tumor cell at least twice.

48. The method of claim 41, wherein said ionizing radiation is contacted with said tumor cell at least twice.

49. A method of treating cancer in a human patient comprising administering chelerythrine to said human patient and administering ionizing radiation to said human patient, wherein the dose of said chelerythrine, when combined with the dose of ionizing radiation, is effective to treat said cancer.

50. The method of claim 49, wherein said cancer is selected from the group consisting of skin cancer, prostate cancer, lung cancer, brain cancer, breast cancer, ovarian cancer, cervical cancer, liver cancer, pancreatic cancer, colon cancer, stomach cancer and leukemia.

51. The method of claim 49, wherein said dose of chelerythrine is about 0.5 mg/kg to about 10 mg/kg.

52. The method of claim 51, wherein said dose of chelerythrine is about 1 mg/kg to about 4 mg/kg.

53. The method of claim 49, wherein said ionizing radiation is selected from the group consisting of γ-irradiation, x-irradiation, microwave irradiation and ultraviolet irradiation.

54. The method of claim 49, wherein said total dose of ionizing radiation is about 1 Gy to about 80 Gy.

55. The method of claim 54, wherein said total dose of ionizing radiation is about 70 Gy.

56. The method of claim 49, wherein said chelerythrine is contacted with said tumor cell at least twice.

57. The method of claim 49, wherein said ionizing radiation is contacted with said tumor cell at least twice.

58. A method of potentiating the effect of ionizing radiation on a tumor cell comprising contacting said tumor cell with chelerythrine and then contacting said tumor cell with ionizing radiation.

59. The method of claim 58, wherein said tumor is selected from the group consisting of a skin cancer cell, a prostate cancer cell, a lung cancer cell, a brain cancer cell, a breast cancer cell, a ovarian cancer cell, a cervical cancer cell, a liver cancer cell, a pancreatic cancer cell, a colon cancer cell, a stomach cancer cell and a leukemia cell.

60. The method of claim 58, wherein said dose of chelerythrine is about 0.5 mg/kg to about 10 mg/kg.

61. The method of claim 60, wherein said dose of chelerythrine is about 1 mg/kg to about 4 mg/kg.

62. The method of claim 58, wherein said ionizing radiation is selected from the group consisting of γ-irradiation, x-irradiation, microwave irradiation and ultraviolet irradiation.

63. The method of claim 58, wherein said total dose of ionizing radiation is about 1 Gy to about 80 Gy.

64. The method of claim 63, wherein said total dose of ionizing radiation is about 70 Gy.

65. The method of claim 58, wherein said chelerythrine is contacted with said tumor cell at least twice.

66. The method of claim 58, wherein said ionizing radiation is contacted with said tumor cell at least twice.

* * * * *